United States Patent [19]
Pall et al.

[11] Patent Number: 5,616,254

[45] Date of Patent: *Apr. 1, 1997

[54] SYSTEM AND METHOD FOR PROCESSING BIOLOGICAL FLUID

[75] Inventors: David B. Pall, Roslyn Estates; Thomas C. Gsell; Vlado I. Matkovich, both of Glen Cove; Thomas Bormann, Melville, all of N.Y.

[73] Assignee: Pall Corporation, East Hills, N.Y.

[*] Notice: The portion of the term of this patent subsequent to Mar. 31, 2009, has been disclaimed.

[21] Appl. No.: 451,494

[22] Filed: May 26, 1995

Related U.S. Application Data

[63] Continuation of Ser. No. 71,495, Jun. 4, 1993, which is a continuation of Ser. No. 788,787, Nov. 6, 1991, Pat. No. 5,217,627, which is a continuation-in-part of Ser. No. 609,654, Nov. 6, 1990, Pat. No. 5,100,564.

[51] Int. Cl.$^6$ ............... B01D 37/00; B01D 21/26; B01D 39/00; A61M 1/00
[52] U.S. Cl. ............ 210/806; 210/188; 210/252; 210/257.1; 210/295; 210/323.1; 210/435; 210/436; 210/472; 210/505; 210/508; 210/767; 210/782; 210/789; 604/4; 604/5; 604/6; 604/406; 604/408; 604/410
[58] Field of Search .................. 210/188, 252, 210/257.1, 295, 323.1, 435, 436, 472, 483, 496, 503, 505, 508, 446, 782, 767, 789, 806; 422/101; 494/37; 604/4, 5, 6, 406, 408, 410

[56] References Cited

U.S. PATENT DOCUMENTS

| | | |
|---|---|---|
| 2,781,064 | 2/1957 | Dawkins . |
| 3,149,758 | 9/1964 | Bush et al. . |
| 3,364,658 | 1/1968 | Walker . |
| 3,394,533 | 7/1968 | Li et al. ................ 55/337 |

(List continued on next page.)

FOREIGN PATENT DOCUMENTS

| | | |
|---|---|---|
| 1158988 | 12/1983 | Canada . |
| 1249110 | 1/1989 | Canada . |
| 2012677 | 9/1990 | Canada . |
| 0090093 | 10/1983 | European Pat. Off. . |
| 0183057 | 6/1986 | European Pat. Off. . |
| 0243744 | 11/1987 | European Pat. Off. . |
| 0267286 | 5/1988 | European Pat. Off. . |
| 0302722 | 2/1989 | European Pat. Off. . |
| 0329303 | 8/1989 | European Pat. Off. . |
| 0336483 | 10/1989 | European Pat. Off. . |
| 0399083 | 11/1990 | European Pat. Off. . |
| 0414006 | 2/1991 | European Pat. Off. . |

(List continued on next page.)

OTHER PUBLICATIONS

Wiltbank, et al., Transfusion, "Filtration Plasmapheresis In Vivo", vol. 21, No. 5, pp. 502–510 (1981).
Beaudoin, et al., Artificial Organs, "Plasma Filtration in Couette Flow Membrane Devices", vol. 13, No. 1, 1989, pp. 43–51.
van Oudheusden, et al., Ann Clin Biochem, "A Multilayer Membrane . . . Primary Health Care", vol. 28, 1991, pp. 55–59.
International Search Report, PCT/US91/03616, 1991.
"Pall Ultipor® I.V. Filter/Air Eliminator . . . ", Pall Biomedical Products Corporation Brochures, Aug. 1980.

*Primary Examiner*—John Kim
*Attorney, Agent, or Firm*—Leydig, Voit & Mayer

[57] ABSTRACT

A system for collecting and processing donated blood comprises a first porous medium interposed between a blood collection bag and a satellite bag and a second porous medium interposed between the blood collection bag and another satellite bag. The porous media are leucocyte depletion media. The system may also include one or more of the following: a red cell barrier medium, a separation medium, a gas inlet, and a gas outlet. The system can be used to centrifuge whole blood into one or more components, and includes a means for protecting the system during centrifugation.

64 Claims, 9 Drawing Sheets

U.S. PATENT DOCUMENTS

| | | | |
|---|---|---|---|
| 3,523,408 | 8/1970 | Rosenberg . | |
| 3,610,418 | 10/1971 | Calderwood | 210/336 |
| 3,623,610 | 11/1971 | Olsen et al. | 210/336 |
| 3,631,654 | 1/1972 | Riely et al. . | |
| 3,650,093 | 3/1972 | Rosenberg . | |
| 3,705,100 | 12/1972 | Blatt et al. . | |
| 3,803,810 | 4/1974 | Rosenberg . | |
| 3,892,236 | 7/1975 | Djerassi . | |
| 4,075,091 | 2/1978 | Bellhouse . | |
| 4,111,199 | 9/1978 | Djerassi | 604/6 |
| 4,126,558 | 11/1978 | Luceyk | 210/429 |
| 4,130,642 | 12/1978 | Kikugawa et al. . | |
| 4,136,796 | 1/1979 | Dubois et al. . | |
| 4,178,248 | 12/1979 | Porter et al. | 210/167 |
| 4,212,742 | 7/1980 | Solomon et al. | 210/247 |
| 4,223,695 | 9/1980 | Muetterties . | |
| 4,276,170 | 6/1981 | Vaillancourt | 210/436 |
| 4,294,594 | 10/1981 | Sloane, Jr. et al. . | |
| 4,322,298 | 3/1982 | Persidsky | 210/787 |
| 4,330,410 | 5/1982 | Takenaka et al. | 210/767 |
| 4,360,435 | 11/1982 | Bellamy et al. | 210/636 |
| 4,381,775 | 5/1983 | Nosé et al. | 604/6 |
| 4,411,866 | 10/1983 | Kanno | 422/25 |
| 4,416,777 | 11/1983 | Kuroda et al. | 210/446 |
| 4,447,220 | 5/1984 | Eberle | 494/26 |
| 4,459,139 | 7/1984 | Vonreis et al. . | |
| 4,543,084 | 9/1985 | Bailey | 494/20 |
| 4,596,657 | 6/1986 | Wisdom | 210/206 |
| 4,604,208 | 8/1986 | Chu et al. | 210/636 |
| 4,619,639 | 10/1986 | Nosé et al. | 604/6 |
| 4,636,309 | 1/1987 | Bellhouse | 210/356 |
| 4,636,310 | 1/1987 | Bellhouse | 210/456 |
| 4,639,243 | 1/1987 | Schmidt et al. | 604/6 |
| 4,675,117 | 6/1987 | Neumann et al. | 210/789 |
| 4,680,025 | 7/1987 | Kruger et al. | 604/6 |
| 4,714,457 | 12/1987 | Alterbaum | 494/20 |
| 4,734,269 | 3/1988 | Clarke et al. | 210/422 |
| 4,746,436 | 5/1988 | Kopp et al. | 210/637 |
| 4,753,733 | 6/1988 | Ramstack | 210/636 |
| 4,753,739 | 6/1988 | Noble | 210/787 |
| 4,767,541 | 8/1988 | Wisdom | 210/749 |
| 4,769,150 | 9/1988 | Ramstack | 210/636 |
| 4,789,473 | 12/1988 | Mathieu et al. | 210/321.8 |
| 4,800,022 | 1/1989 | Leonard | 210/636 |
| 4,806,247 | 2/1989 | Schoendorfer et al. | 210/360.1 |
| 4,810,378 | 3/1989 | Carmen et al. | 210/26 |
| 4,845,132 | 7/1989 | Masuoka et al. | 210/490 |
| 4,855,063 | 8/1989 | Carmen et al. | 210/749 |
| 4,880,548 | 11/1989 | Pall et al. | 210/767 |
| 4,888,115 | 12/1989 | Marinaccio et al. | 210/636 |
| 4,892,668 | 1/1990 | Harmony et al. | 210/782 |
| 4,898,573 | 2/1990 | Takenaka et al. | 604/6 |
| 4,900,308 | 2/1990 | Verkaart | 604/126 |
| 4,909,949 | 3/1990 | Harmony et al. | 210/513 |
| 4,915,847 | 4/1990 | Dillon et al. | 210/737 |
| 4,915,848 | 4/1990 | Carmen et al. | 210/749 |
| 4,919,823 | 4/1990 | Wisdom | 210/749 |
| 4,923,620 | 5/1990 | Pall | 210/767 |
| 4,925,572 | 5/1990 | Pall | 210/767 |
| 4,933,092 | 6/1990 | Aunet et al. | 210/729 |
| 4,943,287 | 7/1990 | Carmen | 604/408 |
| 4,980,297 | 12/1990 | Haynes et al. | 436/178 |
| 4,985,153 | 1/1991 | Kuroda et al. | 210/782 |
| 4,995,967 | 2/1991 | Van Driessche | 210/94 |
| 4,997,577 | 3/1991 | Stewart | 210/767 |
| 5,008,012 | 4/1991 | Hagihara et al. | 210/321.8 |
| 5,013,437 | 5/1991 | Trimmer et al. | 210/321.78 |
| 5,049,268 | 9/1991 | Kopf | 210/231 |
| 5,069,789 | 12/1991 | Mohn et al. | 210/321.84 |
| 5,074,839 | 12/1991 | Choksi et al. | 604/4 |
| 5,079,168 | 1/1992 | Amiot | 437/284 |
| 5,100,564 | 3/1992 | Pall et al. | 210/782 |
| 5,102,407 | 4/1992 | Carmen et al. | 604/4 |
| 5,126,054 | 6/1992 | Matkovich | 210/641 |
| 5,152,905 | 10/1992 | Pall et al. | 210/767 |
| 5,180,504 | 1/1993 | Johnson et al. | 210/767 |
| 5,217,627 | 6/1993 | Pall et al. | 210/767 |
| 5,229,012 | 7/1993 | Pall et al. | 210/767 |
| 5,258,126 | 11/1993 | Pall et al. | 210/767 |
| 5,258,127 | 11/1993 | Gsell et al. | 210/767 |
| 5,266,219 | 11/1993 | Pall et al. | 210/767 |
| 5,334,315 | 8/1994 | Matkovich et al. | 210/641 |
| 5,364,526 | 11/1994 | Matkovich et al. | 210/206 |
| 5,403,304 | 4/1995 | Ishida | 604/403 |
| 5,451,321 | 9/1995 | Matkovich | 210/641 |

FOREIGN PATENT DOCUMENTS

| | | |
|---|---|---|
| 0446713 | 9/1991 | European Pat. Off. . |
| 0455215 | 11/1991 | European Pat. Off. . |
| 0464707 | 1/1992 | European Pat. Off. . |
| 0531540 | 3/1993 | European Pat. Off. . |
| 8903605 | 8/1989 | Germany . |
| 53-100977 | 9/1978 | Japan . |
| 53-122296 | 10/1978 | Japan . |
| 58-174131 | 11/1983 | Japan . |
| 60-53156 | 3/1985 | Japan . |
| 61-215710 | 9/1986 | Japan . |
| 61-253071 | 11/1986 | Japan . |
| 62-236555 | 10/1987 | Japan . |
| 263470 | 3/1990 | Japan . |
| 1221625 | 2/1971 | United Kingdom . |
| 1585989 | 3/1981 | United Kingdom . |
| 7901121 | 12/1979 | WIPO . |
| 8602825 | 5/1986 | WIPO . |
| 8605410 | 9/1986 | WIPO . |
| 8904197 | 5/1989 | WIPO . |
| 9102555 | 3/1991 | WIPO . |
| 9104088 | 4/1991 | WIPO . |
| 9117809 | 11/1991 | WIPO . |
| 9207656 | 5/1992 | WIPO . |
| 9220383 | 11/1992 | WIPO . |
| 9308904 | 5/1993 | WIPO . |
| 9325295 | 12/1993 | WIPO . |

SYSTEM AND METHOD FOR PROCESSING BIOLOGICAL FLUID

This disclosure is a continuation application of prior Ser. No. 08/071,495, filed Jun. 4, 1993, which is a continuation of Ser. No. 07/788,787, filed Nov. 6, 1991, of David B. PALL, THOMAS C. GSELL, VLADO I. MATKOVICH and THOMAS BORMANN for SYSTEM AND METHOD FOR PROCESSING BIOLOGICAL FLUID, which issued as U.S. Pat. No. 5,217,627 on Jun. 8, 1993, which is a continuation-in-part of Ser. No. 07/609,654, filed Nov. 6, 1990, now U.S. Pat. No. 5,100,564.

TECHNICAL FIELD

This invention relates to a system for processing blood donated for the purpose of therapeutic transfusion of blood components and, particularly, to improved methods and apparatuses for preparing, from the donated whole blood, platelet-rich plasma (hereinafter PRP), packed red cells (hereinafter PRC), platelet concentrate (hereinafter PC), and plasma. This invention also relates to a biological fluid processing system for processing biological fluid into its various components.

BACKGROUND OF THE INVENTION

The development of plastic blood collection bags has facilitated the separation of donated whole blood into its various components and analogous products, thereby making these different blood products (e.g., platelet concentrates) available as a transfusion product.

With the passage of time and accumulation of research and clinical data, transfusion practices have changed greatly. One aspect of current practice is that whole blood is rarely administered; rather, patients needing red blood cells are given packed red cells, patients needing platelets are given platelet concentrate, and patients needing plasma are given plasma.

For this reason, the separation of blood into components has substantial therapeutic and monetary value. This is nowhere more evident than in treating the increased damage to a patient's immune system caused by the higher doses and stronger drugs now used during chemotherapy for cancer patients. These more aggressive chemotherapy protocols are directly implicated in the reduction of the platelet content of the blood to abnormally low levels; associated internal and external bleeding additionally requires more frequent transfusions of PC, and this has put pressure on blood banks to increase the platelet yield per unit of blood.

A typical component separation procedure used in the United States, the citrate-phosphate-dextrose-adenine (CPDA-1) system, utilizes a series of steps to separate donated blood into three components, each component having substantial therapeutic and monetary value. The procedure typically utilizes a blood collection bag which is integrally attached via flexible tubing to at least one, and preferably two or more, satellite bags. Using centrifugation, whole blood may be separated by differential sedimentation into such valuable blood components as plasma, packed red cells (PRC), platelets suspended in clear plasma (platelet-rich plasma, or PRP), platelet concentrate (PC), and cryoprecipitate (which may require extra processing).

A typical whole blood collection and processing procedure may include the following:

(1) A unit of donated whole blood (about 450 ml in United States practice) is collected from the donor's vein directly into the blood collection bag which contains the nutrient and anti-coagulant containing CPDA-1.

(2) The blood collection bag is centrifuged (slow speed, or "soft-spin" centrifugation) together with its satellite bags, thereby concentrating the red cells as PRC in the lower portion of the blood collection bag and leaving in the upper portion of the bag a suspension of PRP.

(3) The blood collection bag is transferred, with care not to disturb the interface between the supernatant PRP layer and the sedimented PRC layer, into a device known as a "plasma extractor." The plasma extractor or expressor typically includes front and back plates; the two plates are hinged together at their lower ends and spring biased toward each other such that a pressure of about 90 millimeters of mercury is developed within the bag.

With the blood collection bag positioned between the two plates, a valve, seal or a closure in or on the flexible tubing is opened allowing the supernatant PRP to flow into a first satellite bag. As the PRP flows out of the blood collection bag, the interface with the PRC rises. In current practice, the operator must closely observe the position of the interface as it rises and clamp off the connecting tube when, in his judgment, as much PRP has been transferred as is possible, without allowing red cells to enter the first satellite bag. This is a labor intensive and time consuming operation during which the operator must visually monitor the bag and judiciously and arbitrarily ascertain when to shut-off the connecting tube.

The blood collection bag, now containing only PRC, may be detached and stored at 4° C. until required for transfusion into a patient, or a valve or seal in the tubing may be opened so that the PRC may be transferred to a satellite bag using either the pressure generated by the plasma extractor, or by placing the blood collection apparatus in a pressure cuff, or by elevation to obtain gravity flow.

(4) The PRP-containing satellite bag, together with another satellite bag, is then removed from the extractor and centrifuged at an elevated G force (high speed or "hard-spin" centrifugation) with the time and speed adjusted so as to concentrate the platelets into the lower portion of the PRP bag. When centrifugation is complete, the PRP bag contains sedimented platelets in its lower portion and clear plasma in its upper portion.

(5) The PRP bag is then placed in the plasma extractor, and most of the clear plasma is expressed into a satellite bag, leaving the PRP bag containing only the sedimented platelets and about 50 ml of plasma; then in a subsequent step, this platelet composition is dispersed to make platelet concentrate (PC). The PRP bag, now containing a PC product, is then detached and stored for up to five days at 20°–24° C., until needed for a transfusion of platelets. Multiple units of platelets (e.g., from 6–10 donors, if for transfusion into an adult patient) may be pooled into a single platelet transfusion.

(6) The plasma in the satellite bag may itself be transfused into a patient, or it may be separated by complex processes into a variety of other valuable products.

Commonly used systems other than CPDA-1 include Adsol, Nutricell, and SAG-M. In these latter systems, the collection bag contains only anti-coagulant, and the nutrient solution may be preplaced in a satellite bag. This nutrient solution is transferred into the PRC after the PRP has been separated from the PRC, thereby achieving a higher yield of plasma and longer storage life for the PRC.

In view of this, there is a growing need for an efficient system and method for separating a biological fluid (e.g., whole blood) into its components. Blood bank personnel have responded to the increased need for blood components by attempting to increase PRC and PC yields in a variety of ways. In separating the PRC and PRP fractions (e.g., step 3 above), blood bank personnel have attempted to express more PRP prior to stopping flow from the blood collection bag, but this has often proved to be counterproductive, since the PRP, and the PC subsequently extracted from it, are frequently contaminated by red cells, giving a pink or red color to the normally light yellow PC. The presence of red cells in PC is so highly undesirable that pink or red PC is frequently discarded, or subjected to recentrifugation, both of which increase operating costs and are labor intensive. As a result, blood bank personnel must err on the side of caution by stopping the flow of PRP before it has been fully expressed. Thus, the PC is uncontaminated, but the unexpressed plasma, which is valuable, may be wasted.

This reflects another problem when attempting to increase the yield of individual blood components. While each component is valuable, any savings resulting from increasing the yield may be offset by the increased labor cost, if the operator of the processing system must continuously and carefully monitor the system to increase the yield.

The devices and methods of this invention alleviate the above-described problems and, in addition, provide a higher yield of superior quality PRC and PC.

The separation of the various blood components using centrifugation is attended by a number of other problems. For example, when PRP is centrifuged to obtain a layer consisting principally of platelets concentrated at the bottom of the PRP-containing bag, e.g., step 4 above, the platelets so concentrated tend to form a dense aggregate which must be dispersed in plasma to form platelet concentrate. The dispersion step is usually carried out by gentle mixing, for example, by placing the bag on a moving table which rotates with a processing tilted motion. This mixing requires several hours, a potentially undesirable delay, and is believed by many researchers to produce a partially aggregated platelet concentrate. It is further believed that the platelets may be damaged by the forces applied during centrifugation.

Finally, a problem attendant with the separation of various blood components using a multiple bag system and centrifugation is that highly valuable blood components become trapped in the conduits connecting the various bags and in the various devices that may be used in the system.

Conventional processing and storage techniques may also present problems. For example, air, in particular oxygen, present in stored blood and blood components, or in the storage container, may lead to an impairment of the quality of the blood components, and may decrease their storage life. More particularly, oxygen may be associated with an increased metabolic rate (during glycolysis), which may lead to decreased storage life, and decreased viability and function of whole blood cells. For example, during storage red blood cells metabolize glucose, producing lactic and pyruvic acids. These acids decrease the pH of the medium, which in turn decreases metabolic functions. Furthermore, the presence of air or gas in the satellite bag may present a risk when a patient is transfused with a blood component. For example, as little as 5 ml of air or gas may cause severe injury or death. Despite the deleterious effect of oxygen on storage life and the quality of blood and blood components, the prior art has not addressed the need to remove gases from blood processing systems during collection and processing.

In addition to the above-listed components, whole blood contains white blood cells (known collectively as leucocytes) of various types, of which the most important are granulocytes and lymphocytes. White blood cells provide protection against bacterial and viral infection. The transfusion of blood components which have not been leucocyte-depleted is not without risk to the patient receiving the transfusion. Some of these risks are detailed in U.S. Pat. No. 4,923,620, and in U.S. Pat. No. 4,880,548, which are incorporated herein by reference.

In the above described centrifugal method for separating blood into the three basic fractions, the leucocytes are present in substantial quantities in both the packed red cells and platelet-rich plasma fractions. It is now generally accepted that it is highly desirable to reduce the leucocyte concentration of these blood components to as low a level as possible. While there is no firm criterion, it is generally accepted that many of the undesirable effects of transfusion would be reduced if the leucocyte content were reduced by a factor of about 100 or more prior to administration to the patient. This approximates reducing the average total content of leucocytes in a single unit of PRC to less than about $1\times10^6$, and in a unit of PRP or PC to less than about $1\times10^5$. Devices which have previously been developed in attempts to meet this objective have been based on the use of packed fibers, and have generally been referred to as filters. However, it would appear that processes utilizing filtration based on separation by size cannot succeed for two reasons. First, leucocytes can be larger than about 15 µm (e.g., granulocytes and macrocytes) to as small as 5 to 7 µm (e.g., lymphocytes). Together, granulocytes and lymphocytes represent the major proportion of all of the leucocytes in normal blood. Red blood cells are about 7 µm in diameter, i.e., they are about the same size as lymphocytes, one of the two major classes of leucocytes which must be removed. Secondly, all of these cells deform so that they are able to pass through much smaller openings than their normal size. Accordingly, it has been widely accepted that removal of leucocytes is accomplished mainly by adsorption on the internal surfaces of porous media, rather than by filtration.

Leucocyte depletion is particularly important with respect to a blood component such as PC. Platelet concentrates prepared by the differential centrifugation of blood components will have varying levels of leucocyte contamination related to the time and to the magnitude of the force developed during centrifugation. The level of leucocyte contamination in unfiltered conventional platelet preparations of 6 to 10 pooled units is generally at a level of about $5\times10^8$ or greater. It has been demonstrated that leucocyte removal efficiencies of 81 to 85% are sufficient to reduce the incidence of febrile reactions to platelet transfusions. Several other recent studies report a reduction in alloimmunization and platelet refractoriness at levels of leucocyte contamination below about $1\times10^7$ per unit. For a single unit of PC averaging a leucocyte contamination level (under current practice) of about $7\times10^7$ leucocytes, the goal after filtration is less than $1\times10^4$ leucocytes. The existing studies, therefore, suggest the desirability of at least a two log (99%) reduction of leucocyte contamination. More recent studies suggest that a three log (99.9%) or even a four log (99.99%) reduction would be significantly more beneficial.

An additional desirable criterion is to restrict platelet loss to about 15% or less of the original platelet concentration. Platelets are notorious for being "sticky", an expression reflecting the tendency of platelets suspended in blood plasma to adhere to any non-physiological surface to which they are exposed. Under many circumstances, they also adhere strongly to each other.

In any system which depends upon filtration to remove leucocytes from a platelet suspension, there will be substantial contact between platelets and the internal surfaces of the filter assembly. The filter assembly must be such that the platelets have minimal adhesion to, and are not significantly adversely affected by contact with, the filter assembly's internal surfaces.

If the leucocyte depletion device comprises a porous structure, microaggregates, gels, fibrin, fibrinogen and fat globules tend to collect on or within the pores, causing blockage which inhibits flow. Conventional processes, in which the filter for depleting leucocytes from PRC is preconditioned by passing saline through the filter assembly with or without a post-filtration saline flush, are undesirable because the liquid content of the transfusion is unduly increased, thus potentially overloading the patient's circulatory system with liquid. An objective of an embodiment of this invention is a leucocyte depletion device which removes leucocytes and these other elements with high efficiency and without clogging, requires no preconditioning prior to processing PRC derived from freshly drawn blood, and does not require post-filtration flushing to reclaim red cells remaining in the filter.

Because of the high cost and limited availability of blood components, a device comprising a porous medium used to deplete leucocytes from biological fluid should deliver the highest possible proportion of the component present in the donated blood. An ideal device for the leucocyte depletion of PRC or PRP would be inexpensive, relatively small, and be capable of rapidly processing blood components obtained from about one unit or more of biological fluid (e.g., donated whole blood), in, for example, less than about one hour. Ideally, this device would reduce the leucocyte content to the lowest possible level, while maximizing the yield of a valuable blood component while minimizing an expensive, sophisticated, labor intensive effort by the operator of the system. The yield of the blood component should be maximized while at the same time delivering a viable and physiologically active component—e.g., by minimizing damage due to centrifugation, and/or the presence of air or gas. It may also be preferable that the PRC porous medium be capable of removing platelets, as well as fibrinogen, fibrin strands, tiny fat globules, and other components such as microaggregates which may be present in whole blood.

Definitions

The following definitions are used in reference to the invention:

(A) Blood Product or Biological Fluid: anti-coagulated whole blood (AWB); packed red cells obtained from AWB; platelet-rich plasma (PRP) obtained from AWB; platelet concentrate (PC) obtained from AWB or PRP; plasma obtained from AWB or PRP; red cells separated from plasma and resuspended in physiological fluid; and platelets separated from plasma and resuspended in physiological fluid. Blood product or biological fluid also includes any treated or untreated fluid associated with living organisms, particularly blood, including whole blood, warm or cold blood, and stored or fresh blood; treated blood, such as blood diluted with a physiological solution, including but not limited to saline, nutrient, and/or anticoagulant solutions; one or more blood components, such as platelet concentrate (PC), platelet-rich plasma (PRP), platelet-free plasma, platelet-poor plasma, plasma, or packed red cells (PRC); analogous blood products derived from blood or a blood component or derived from bone marrow. The biological fluid may include leucocytes, or may be treated to remove leucocytes. As used herein, blood product or biological fluid refers to the components described above, and to similar blood products or biological fluids obtained by other means and with similar properties. In accordance with the invention, each of these blood products or biological fluids is processed in the manner described herein.

(B) Unit of Whole Blood: Blood banks in the United States commonly draw about 450 milliliters (ml) of blood from the donor into a bag which contains an anticoagulant to prevent the blood from clotting. However, the amount drawn differs from patient to patient and donation to donation. Herein the quantity drawn during such a donation is defined as a unit of whole blood.

(C) Unit of Packed Red Cells (PRC), Platelet-rich Plasma (PRP) or Platelet Concentrate (PC): As used herein, a "unit" is defined by the United States' practice, and a unit of PRC, PRP, PC, or of red cells or platelets in physiological fluid or plasma, is the quantity derived from one unit of whole blood. It may also refer to the quantity drawn during a single donation. Typically, the volume of a unit varies. For example, the volume of a unit of PRC varies considerably depending on the hematocrit (percent by volume of red cells) of the drawn whole blood, which is usually in the range of about 37% to about 54%. The concomitant hematocrit of PRC, which varies over the range from about 50% to over 80%, depends in part on whether the yield of one or another blood product is to be minimized. Most PRC units are in the range of about 170 to about 350 ml, but variation below and above these figures is not uncommon. Multiple units of some blood components, particularly platelets, may be pooled or combined, typically by combining 6 or more units.

(D) Plasma-Depleted Fluid: A plasma-depleted fluid refers to any biological fluid which has had some quantity of plasma removed therefrom, e.g., the platelet-rich fluid obtained when plasma is separated from PRP, or the fluid which remains after plasma is removed from whole blood.

(E) Porous medium: refers to the porous medium through which one or more blood components or biological fluids pass. The PRC porous medium depletes leucocytes from the packed red cell component. The platelet or PRP porous medium refers generically to any one of the media which deplete leucocytes from the non-PRC blood components, i.e., from PRP or from PC. The red cell barrier medium blocks the passage of red cells and depletes leucocytes from PRP to a greater or lesser degree while allowing the passage of platelets.

As noted in more detail below, the porous medium for use with PRC may be formed from any natural or synthetic fiber (or from other materials of similar surface area and pore size) compatible with blood. The porous medium may remain untreated. Preferably, the critical wetting surface tension (CWST) of the porous medium is within a certain range, as noted below and as dictated by its intended use. The pore surfaces of the medium may be modified or treated in order to achieve the desired CWST. For example, the CWST of a PRC porous medium is typically above about 53 dynes/cm.

The porous medium for use with PRP may be formed from any natural or synthetic fiber or other porous material compatible with blood. The porous medium may remain untreated. Preferably, the CWST and zeta potential of the porous medium are within certain ranges, as disclosed below and as dictated by its intended use. For example, the CWST of a PRP porous medium is typically above about 70 dynes/cm.

The porous media according to the invention may be connected to a conduit interposed between the containers, and may be positioned in a housing which in turn can be connected to the conduit. As used herein, filter assembly refers to the porous medium positioned in a suitable housing. An exemplary filter assembly may include a leucocyte depletion assembly or device or a red cell barrier assembly or device. A biological fluid processing system, such as a blood collection and processing system, may comprise porous media, preferably as filter assemblies. Preferably, the porous medium forms an interference fit at its edges when assembled into the housing.

The porous medium may be configured as a flat sheet, a corrugated sheet, a web, or a membrane. The porous medium may be pre-formed, and configured as hollow fibers, although it is not intended that the invention should be limited thereby.

(F) Separation Medium: A separation medium refers to a porous medium effective for separating one component of a biological fluid from another component. The separation media according to the invention are suitable for passing at least one component of the blood product or biological fluid, particularly plasma, therethrough, but not other components of the blood product or biological fluid, particularly platelets and/or red cells.

As noted in more detail below, the separation medium for use with a biological fluid may be formed from any natural or synthetic fiber or from a porous or permeable membrane (or from other materials of similar surface area and pore size) compatible with a biological fluid. The surface of the fibers or membrane may be unmodified or may be modified to achieve a desired property. Although the separation medium may remain untreated, the fibers or membrane are preferably treated to make them even more effective for separating one component of a biological fluid, e.g., plasma, from other components of a biological fluid, e.g., platelets or red cells. The separation medium is preferably treated in order to reduce or eliminate platelet adherence to the medium. Any treatment which reduces or eliminates platelet adhesion is included within the scope of the present invention. Furthermore, the medium may be surface modified as disclosed in U.S. Pat. No. 4,880,548, incorporated herein by reference, in order to increase the critical wetting surface tension (CWST) of the medium and to be less adherent of platelets. Defined in terms of CWST, a preferred range of CWST for a separation medium according to the invention is above about 70 dynes/cm, more preferably above about 90 dynes/cm. Also, the medium may be subjected to gas plasma treatment in order to reduce platelet adhesion. Preferably, the critical wetting surface tension (CWST) of the separation medium is within a certain range, as noted below and as dictated by its intended use. The pore surfaces of the medium may be modified or treated in order to achieve the desired CWST.

The separation medium may be pre-formed, multi-layered, and/or may be treated to modify the surface of the medium. If a fibrous medium is used, the fibers may be treated either before or after forming the fibrous lay-up. It is preferred to modify the fiber surfaces before forming the fibrous lay-up because a more cohesive, stronger product is obtained after hot compression to form an integral filter element. The separation medium is preferably pre-formed.

The separation medium may be configured in any suitable fashion, such as a flat sheet, a corrugated sheet, a web, hollow fibers, or a membrane.

(G) Voids volume is the total volume of all of the pores within a porous medium. Voids volume is expressed hereinafter as a percentage of the apparent volume of the porous medium.

(H) Measurement of fiber surface area and of average fiber diameter: In accordance with the invention, a useful technique for the measurement of fiber surface area, for example by gas adsorption, is generally referred to as the "BET" measurement. The surface area of melt blown webs can be used to calculate average fiber diameter, using PBT as an example:

$$\text{Total volume of fiber in 1 gram} = \frac{1}{1.38} \text{ cc}$$

(where 1.38 = fiber density of PBT, g/cc)

$$\text{hence } \frac{\pi d^2 L}{4} = \frac{1}{1.38} \quad (1)$$

$$\text{Area of the fiber is } \pi dL = A_f \quad (2)$$

$$\text{Dividing (1) by (2), } \frac{d}{4} = \frac{1}{1.38 A_f}$$

$$\text{and } d = \frac{4}{1.38 A_f} = \frac{2.9}{A_f}, \text{ or } (0.345 A_f)^{-1}$$

where
L=total length in cm of 1 gram of fiber,
d=average fiber diameter in centimeters, and
$A_f$=fiber surface area in cm²/g.
If the units of d are micrometers, the units of $A_f$ become M²/g (square meters/gram), which will be used hereinafter.

(I) Critical Wetting Surface Tension: As disclosed in U.S. Pat. No. 4,880,548, the CWST of a porous medium may be determined by individually applying to its surface a series of liquids with surface tensions varying by 2 to 4 dynes/cm and observing the absorption or non-absorption of each liquid over time. The CWST of a porous medium, in units of dynes/cm, is defined as the mean value of the surface tension of the liquid which is absorbed and that of the liquid of neighboring surface tension which is not absorbed within a predetermined amount of time. The absorbed and non-absorbed values depend principally on the surface characteristics of the material from which the porous medium is made and secondarily on the pore size characteristics of the porous medium.

Liquids with surface tensions lower than the CWST of a porous medium will spontaneously wet the medium on contact, and, if the pores of the medium are interconnected, liquid will flow through the medium readily. Liquids with surface tensions higher than the CWST of the porous medium may not flow at all at low differential pressures, or may flow unevenly at sufficiently high differential pressures to force the liquid through the porous medium. In order to achieve adequate priming of a fibrous medium with a liquid such as blood, the fibrous medium preferably has a CWST in the range of about 53 dynes/cm or higher.

For the porous medium which is used to process PRC, it is preferred that the CWST be held within a range somewhat above the CWST of untreated polyester fiber (52 dynes/cm), for example, above about 53 dynes/cm, more preferably, above about 60 dynes/cm. For the porous medium which is used to process PRP, it is preferred that the CWST be held within a range above about 70 dynes/cm.

(J) General procedure for measuring zeta potential: Zeta potential was measured using a sample cut from a ½ inch thick stack of webs.

The zeta potential was measured by placing the sample in an acrylic filter holder which held the sample snugly between two platinum wire screens 100×100 mesh (i.e., 100 wires in each direction per inch). The meshes were connected, using copper wire, to the terminals of a Triplett Corporation model 3360 Volt-Ohm Meter, the mesh on the upstream side of the sample being connected to the positive terminal of the meter. A pH-buffered solution was flowed through the sample using a differential pressure of 45 inches of water column across the filter holder and the effluent was collected. For measurements at pH 7, a buffered solution was made by adding 6 ml pH 7 buffer (Fisher Scientific Co. catalog number SB108-500) and 5 ml pH 7.4 buffer (Fisher Scientific Co. catalog number SB110-500) to 1 liter pyrogen-free deionized water. For measurements at pH 9, a buffered solution was made by adding 6 ml pH 9 buffer (Fisher Scientific Co. catalog number SB114-500) and 2 ml pH 10 buffer (Fisher Scientific Co. catalog number SB116-500) to 1 liter pyrogen-free deionized water. The electrical potential across the filter holder was measured during flow (it required about 30 seconds of flow for the potential to stabilize) and was corrected for cell polarization by substracting from it the electrical potential measured when flow was stopped. During the period of flow the pH of the liquid was measured using a Cole-Parmer model J-5994-10 pH meter fitted with an in-line model J-5993-90 pH probe. The conductivity of the liquid was measured using a Cole-Parmer model J-1481-60 conductivity meter fitted with a model J-1481-66 conductivity flow cell. Then the polarity of the volt meter was reversed, and the effluent was flowed backwards through the filter holder using a differential pressure of 45 inches of water column. As in the first instance the electrical potential measured during flow was corrected for cell polarization by subtracting from it the electrical potential measured after flow was stopped. The average of the two corrected potentials was taken as the streaming potential.

The zeta potential of the medium was derived from the streaming potential using the following relationship (J. T. Davis et al., *Interfacial Phenomena*, Academic Press, New York, 1963):

$$\text{Zeta Potential} = \frac{4\pi^n}{DP} \cdot E_s \lambda$$

where $^n$ is the viscosity of the flowing solution, D is its dielectric constant, $\lambda$ is its conductivity, $E_s$ is the streaming potential and P is the pressure drop across the sample during the period of flow. In these tests the quantity $4\pi^n/DP$ was equal to 0.800.

(K) Tangential flow filtration: As used herein, tangential flow filtration refers to passing or circulating a biological fluid in a generally parallel or tangential manner to the surface of the separation medium.

SUMMARY OF THE INVENTION

In the devices and methods of this invention, leucocyte depletion of a biological fluid (e.g., PRC or PRP) is carried out at the time of processing, which, in the United States, is generally within about 6 to 8 hours of the time the blood is drawn. Thus, as a biological fluid is transferred from the bag in which it is contained, leucocytes are removed by the appropriate porous medium, and leucocyte-depleted biological fluid is collected in the satellite bag. In accordance with the invention, a system is provided whereby a biological fluid such as whole blood is processed to form PRP and PRC. PRP is leucocyte depleted by interposing between the blood collection bag and a first satellite bag at least one porous medium for depleting leucocytes from PRP; PRC is leucocyte depleted by interposing between the blood collection bag and a second satellite bag at least one porous medium for removing leucocytes from PRC.

The invention also comprises a centrifugation system wherein one (or both) of the interposed leucocyte depletion filter assemblies is (are) cooperatively arranged with a centrifuge bucket in a manner such that the filter assembly, the porous medium in the filter assembly, and the blood bags are not damaged by the very large forces generated during the centrifugation process.

Processes and systems according to the invention may also include a red cell barrier medium that allows the passage of one component of the biological fluid, but prevents the passage of another component through the medium, thereby eliminating the need for continuous monitoring by an operator and increasing the efficiency with which a biological fluid such as whole blood is separated into one or more components.

Additionally, processes and systems according to the invention may include a gas outlet that allows gas that may be present in the system out of the system.

Processes and systems according to the invention may also include a gas inlet that allows gas into the system to recover a biological fluid that may be entrapped or retained during processing.

The invention also involves the treatment of a biological fluid to non-centrifugally separate at least one component from the biological fluid, e.g., treating PRP to obtain plasma and PC, or separating plasma from whole blood. Processes and devices according to the invention utilize a separation medium that allows the passage of one component of the biological fluid, such as plasma, but prevents passage of other components, such as platelets or red cells, through the medium, thereby eliminating the need for "hard-spin" centrifugation as a processing step. Tangential flow of a biological fluid parallel to the upstream surface of the separating medium permits the passage of plasma through the medium, while reducing the tendency for cellular components or platelets to adhere to the surface of the medium, thus assisting in the prevention of passage of platelets through the separation medium. The hydrodynamics of flow parallel to a surface are indeed believed to be such that during flow parallel to the surface, platelets develop a spin which causes them to be recovered from the surface.

SPECIFIC DESCRIPTION OF THE INVENTION

Figure 1:
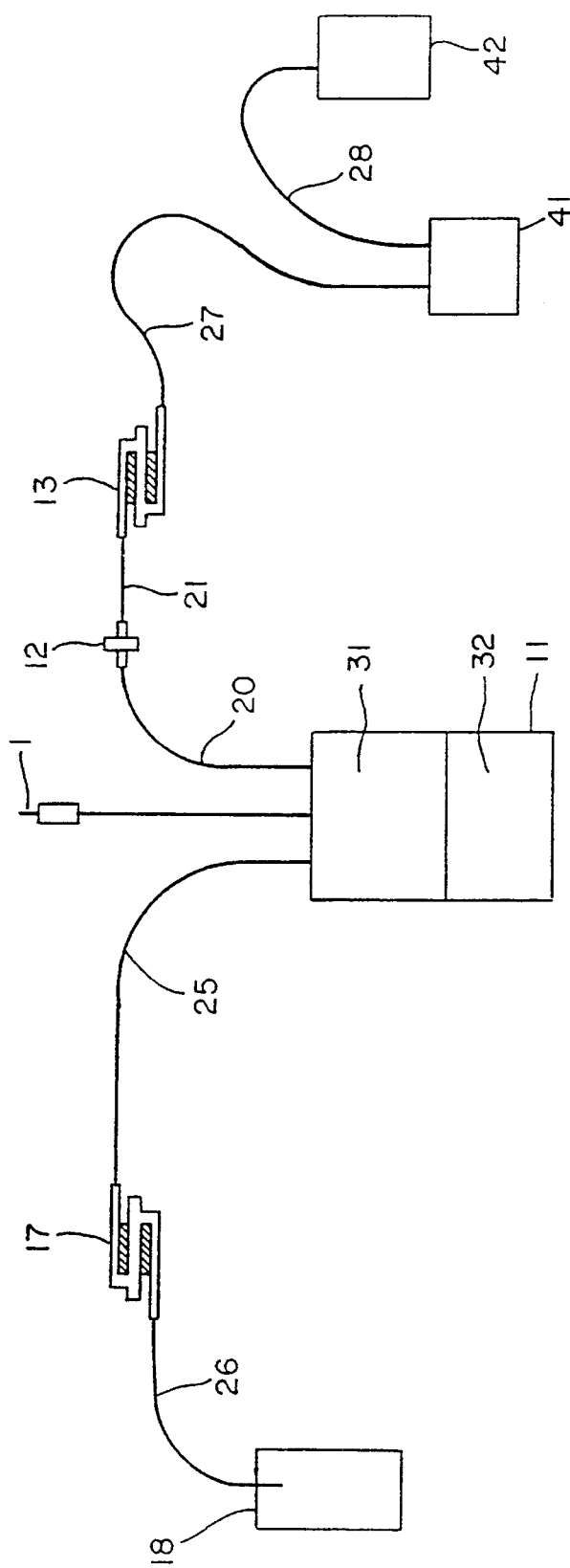
FIG. 1 is an embodiment of a biological fluid processing system according to the invention, whereby biological fluid is separated into components by centrifugal separation.

The present invention involves a biological fluid, preferably blood, collection and processing assembly comprising a first container and a second container, and a conduit interconnecting the first container with the second container; and at least one third container and a conduit interconnecting the first container with the third container; and having interposed between the first container and a second container, at least one first porous medium; and having interposed between the first container and a third container, at least one second porous medium. The first porous medium may be a leucocyte depletion medium, a red cell barrier medium, an assembly comprising a leucocyte depletion medium and a red cell barrier medium, or combinations thereof. The second porous medium may be a leucocyte depletion medium which may, optionally, include a microaggregate filter element and/or a gel pre-filter element. As shown in more detail below, the assembly may also include additional containers, porous media, and conduits interconnecting the containers and porous media.

In another embodiment of the invention, the blood collection and processing assembly comprises containers interconnected with a conduit, and a porous medium interposed in the conduit for depleting leucocytes from PRC wherein the porous medium has a CWST greater than about 53 dynes/cm.

In another embodiment of the invention, the blood collection and processing assembly comprises containers interconnected with a conduit, and a porous medium interposed in the conduit for depleting leucocytes from PRP wherein the porous medium has a CWST greater than about 70 dynes/cm.

The invention also involves a biological fluid processing system comprising a first container; a first porous medium comprising a red cell barrier medium communicating with the first container, and defining a first flow path; and a second porous medium comprising a leucocyte depletion medium communicating with the first container, and defining a second flow path. As shown in more detail below, the system may also include additional containers, flow paths, and porous media.

The invention also involves a method for collecting and processing blood comprising collecting whole blood in a container; centrifuging the whole blood; passing the supernatant layer of the centrifuged blood through a first porous medium, the first porous medium comprising at least one of a leucocyte depletion medium, a red cell barrier medium, and a combined leucocyte depletion red cell barrier medium; and passing the sediment layer of the centrifuged blood through a second porous medium, the second porous medium comprising a leucocyte depletion medium.

The invention also involves a method for processing a biological fluid comprising expressing a biological fluid from a first container to a first porous medium comprising a red cell barrier medium; and expressing a biological fluid from the first container to a second porous medium. As shown in more detail below, the method may also include processing the fluid through additional containers, flow paths, and porous media.

An exemplary biological fluid collection and processing system is shown in FIG. 1. The biological fluid processing system is generally denoted as 10. It may comprise a first container or collection bag 11; a needle or cannula 1 adapted to be inserted into the donor; an optional red cell barrier assembly 12; a first leucocyte depletion assembly 13; a second container (first satellite bag) 41; an optional fourth container (third satellite bag) 42; a second leucocyte depletion assembly 17; and a third container (second satellite bag) 18. Each of the assemblies or containers may be in fluid communication through tubing, preferably flexible tubing, 20, 21, 25, 26, 27 or 28. The first leucocyte depletion assembly preferably includes a porous medium for passing PRP; the second leucocyte depletion assembly preferably includes a porous medium suitable for passing PRC. A seal, valve, clamp, or transfer leg closure or cannula (not illustrated) may also be positioned in or on the tubing or in the collection and/or satellite bags. The seal (or seals) is opened when fluid is to be transferred between bags.

Figure 2:
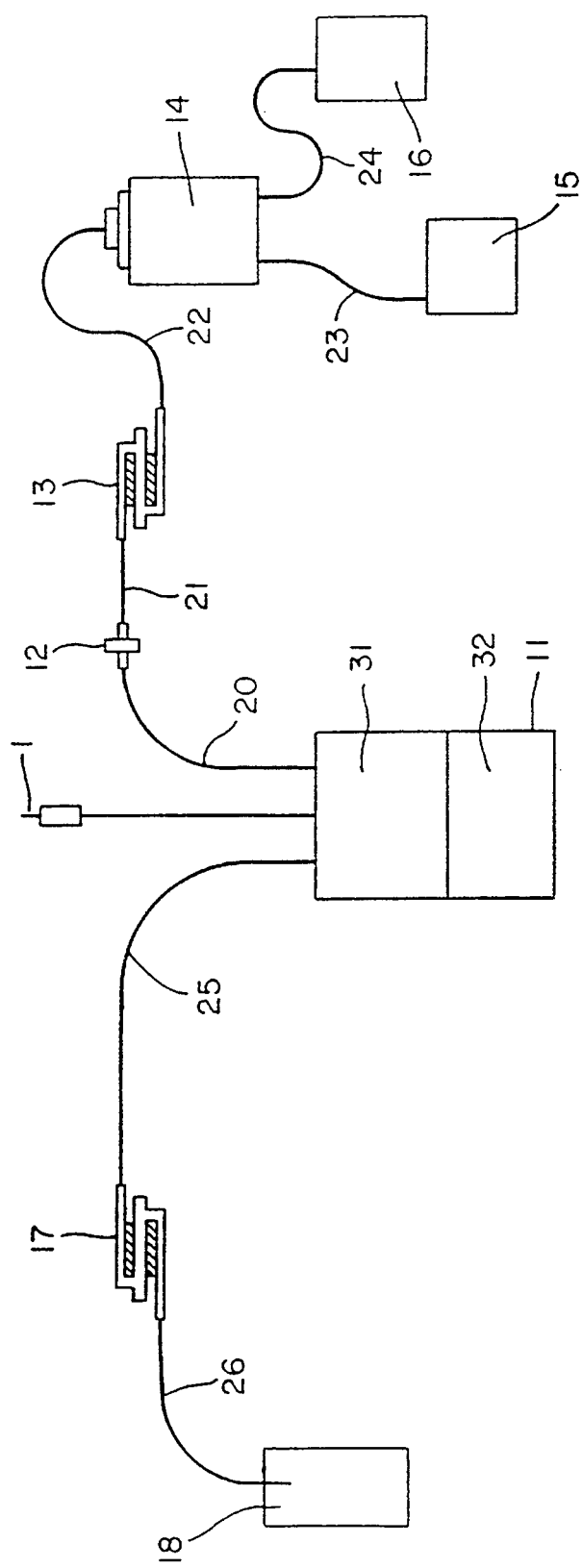
FIG. 2 is another embodiment of a biological fluid processing system according to the invention, including a non-centrifugal separation device.

In another exemplary configuration, the blood processing system shown in FIG. 2 is the same as the exemplary system shown in FIG. 1, except that the portion of the system downstream of leucocyte depletion assembly 13 includes a separation assembly 14, preferably a non-centrifugal separation assembly.

Figure 3:
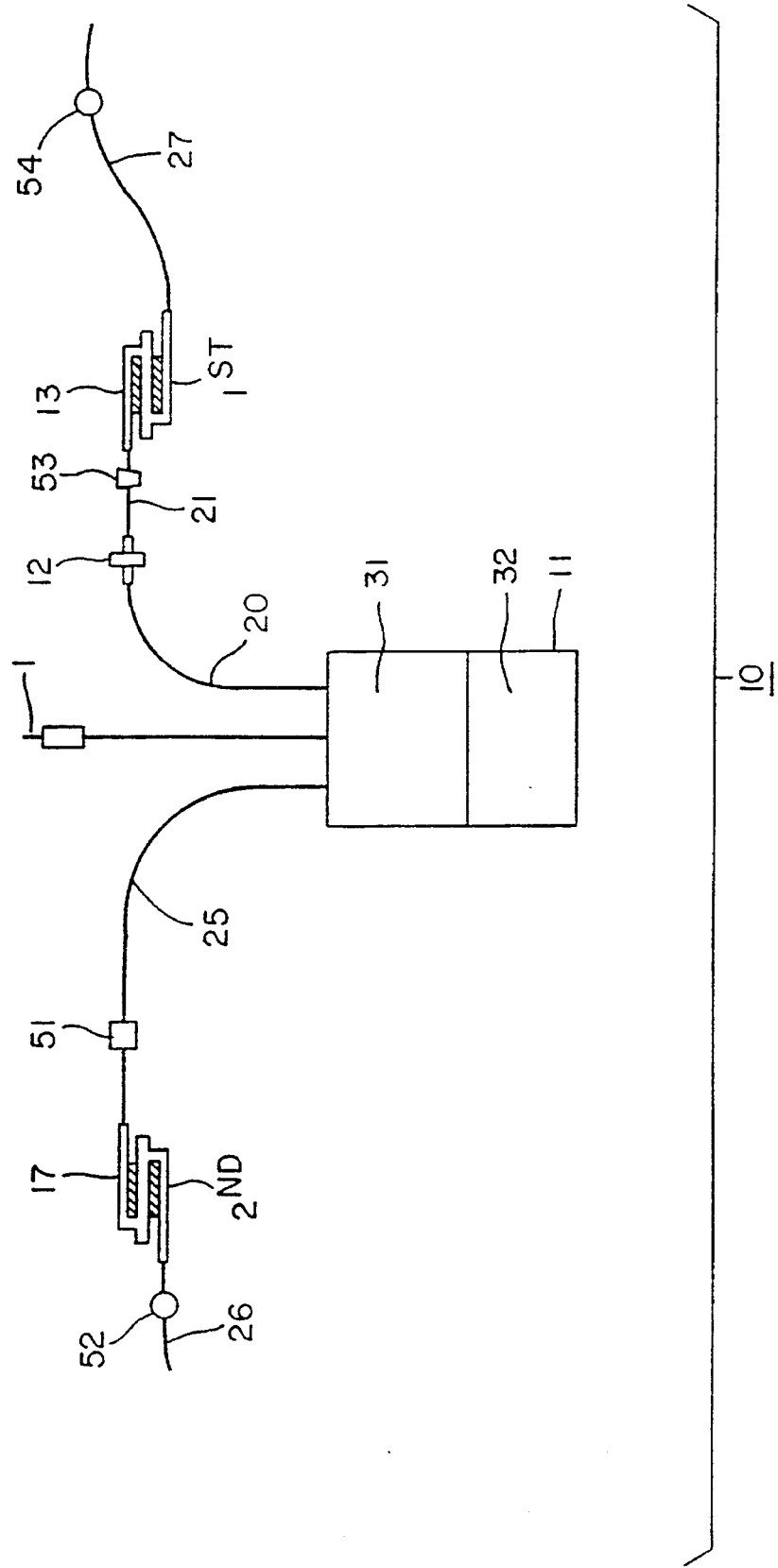
FIG. 3 is an embodiment of the invention which incorporates a gas inlet and a gas outlet.

In another exemplary configuration, shown in FIG. 3, the invention may also comprise at least one gas inlet 51, 53 and/or at least one gas outlet 52, 54. The system of FIG. 3 includes a first container or collection bag 11 in fluid communication with an optional red cell barrier assembly 12, gas inlet 53, a leucocyte depletion assembly 13, and gas outlet 54. First container 11 may also be in fluid communication with a gas inlet 51, a leucocyte depletion assembly 17, and a gas outlet 52. As shown in more detail below, the assembly may also include additional containers, flow paths, and porous media.

Any number and combinations of assemblies, porous media, containers, and conduits are suitable. One skilled in the art will recognize that the invention as described here may be reconfigured into different combinations, which are included within the scope of the invention.

Each of the components of the assembly will now be described in more detail below.

The containers which are used in the biological fluid processing assembly may be constructed of any material compatible with a biological fluid, such as whole blood or a blood component, and capable of withstanding a centrifugation and sterilization environment. A wide variety of these containers are already known in the art. For example, blood collection and satellite bags are typically made from plasticized polyvinyl chloride, e.g. PVC plasticized with dioctylphthalate, diethylhexylphthalate, or trioctyltrimellitate. The bags may also be formed from polyolefin, polyurethane, polyester, and polycarbonate.

As used herein, the tubing may be any conduit or means which provides fluid communication between the containers, and is typically made from the same flexible material as is used for the containers, preferably plasticized PVC. The tubing may extend into the interior of the container, and may be used as a siphon, for example. There may be a number of tubes providing fluid communication to any individual container, and the tubes may be oriented in a number of ways. For example, there may be at least two tubes oriented at the top of the collection bag, or at the bottom of the bag, or a tube at each end of the bag.

Additionally, the tubes, assemblies, porous media, and containers, may be oriented to define different flow paths.

For example, when whole blood is processed, the PRP may flow along a first flow path, e.g., through the red cell barrier assembly (if present), a PRP leucocyte depletion assembly, and into a satellite bag (e.g., a second container). Similarly, the PRC may flow along a second flow path, e.g., through the PRC leucocyte depletion assembly, and into a satellite bag (e.g., a third container). Since independent flow paths may be present, biological fluids (e.g., PRP and PRC) may flow concurrently, or sequentially.

A seal, valve, clamp, transfer leg closure, or the like is typically located in or on the tubing. It is intended that the present invention is not limited by the type of material used to construct the containers or the conduit which connects the containers.

The composition of the various porous media will depend in part on the function desired, e.g., red blood cell blockage or leucocyte depletion. A preferred composition of the various porous media is a mat or web composed of fibers, which are preferably thermoplastic. The fibers of the porous media may comprise any fiber compatible with biological fluid, and may be either natural or synthetic fibers. In accordance with the invention, the fibers are preferably treated or modified in order to achieve or increase the CWST. For example, the fibers may be surface modified to increase the critical wetting surface tension (CWST) of the fibers. For example, the treated or untreated fibers used in the PRC porous medium preferably have a CWST above about 53 dynes/cm; for the PRP porous medium, above about 70 dynes/cm. Also, the fibers may be bonded, fused, or otherwise fixed to one another, or they may be mechanically entwined. Other porous media, for example, open cell foamed plastics, surface modified as noted above, may be similarly used.

While the porous media can be produced from any material compatible with biological fluid, practical consideration dictate that consideration be given first to the use of commercially available materials. The porous media of this invention may be preferably formed, for example, from any synthetic polymer capable of forming fibers and of serving as a substrate for grafting. Preferably, the polymer should be capable of reacting with at least one ethylenically unsaturated monomer under the influence of ionizing radiation without the matrix being significantly or excessively adversely affected by the radiation. Suitable polymers for use as the substrate include, but are not limited to, polyolefins, polyesters, polyamides, polysulfones, acrylics, polyacrylonitriles, polyaramides, polyarylene oxides and sulfides, and polymers and copolymers made from halogenated olefins and unsaturated nitriles. Examples include, but are not limited to, polyvinylidene fluoride, polyethylene, polypropylene, cellulose acetate, and Nylon 6 and 66. Preferred polymers are polyolefins, polyesters, and polyamides. The most preferred polymer is polybutylene terephthalate (PBT).

Surface characteristics of a fiber may remain unmodified, or can be modified by a number of methods, for example, by chemical reaction including wet or dry oxidation; by coating the surface by depositing a polymer thereon; or by grafting reactions wherein the substrate or fiber surface is activated prior to or during wetting of the fiber surface by a monomer solution by exposure to an energy source such as heat, a Van der Graff generator, ultraviolet light, or to various other forms of radiation; or by subjecting the fibers to gas plasma treatment. A preferred method is a grafting reaction using gamma-radiation, for example, from a cobalt source.

An exemplary radiation grafting technique employs at least one of a variety of monomers each comprising an ethylene or acrylic moiety and a second group, which is preferred to be a hydrophilic group (e.g., —COOH, or —OH). Grafting of the fibrous medium may also be accomplished by compounds containing an ethylenically unsaturated group, such as an acrylic moiety, combined with a hydroxyl group, preferably monomers such as hydroxyethyl methacrylate (HEMA), or acrylic acid. The compounds containing an ethylenically unsaturated group may be combined with a second monomer such as methyl acrylate (MA), methyl methacrylate (MMA), or methacrylic acid (MAA). MA or MMA are preferably incorporated into the porous medium used to treat PRC, and MAA is preferably incorporated into the porous medium used to treat the PRP. Preferably, the MAA to HEMA monomer weight ratio in the modifying mixture may be between about 0.01:1 and about 0.5:1; preferably, the MA or MMA to HEMA monomer weight ratio in the modifying mixture may be between about 0.01:1 and about 0.4:1. Use of HEMA contributes to a very high CWST. Analogues with similar functional characteristics may also be used to modify the surface characteristics of fibers.

It has been observed that porous media, surface treated using some grafting monomers or combinations of monomers, behave differently with respect to the span between the surface tension of the liquid which is absorbed and the surface tension of the liquid which is not absorbed when determining the CWST. This span can vary from less than 3 to as much as 20 or more dynes/cm. Preferably, the media has a span between the absorbed and non-absorbed values of about 5 or fewer dynes/cm. This choice reflects the greater precision with which the CWST can be controlled when narrower spans are selected, albeit media with wider spans may also be used. The use of the narrower span is preferred in order to improve product quality control.

Radiation grafting may increase fiber-to-fiber bonding in a fibrous medium. Consequently, a fibrous medium which exhibits little or no fiber-to-fiber bonding in an untreated stats may exhibit significant fiber-to-fiber bonding after the fibers have been radiation grafted to increase the CWST of the medium.

For the porous media for use with a biological fluid such as PRP, a preferred range for the CWST of the fiber is preferably above about 70 dynes/cm, typically about 70 to 115 dynes/cm; a more preferred range is 90 to 100 dynes/cm, and a still more preferred range is 93 to 97 dynes/cm. A preferred range for the sets potential (at the pH of plasma (7.3)) is about −3 to about −30 millivolts, a more preferred range is about −7 to about −20 millivolts, and a still more preferred range is about −10 to about −14 millivolts.

In packed red cells, as well as in whole blood, the red cells are suspended in blood plasma, which has a surface tension of about 73 dynes/cm. For the depletion of the leucocyte content of PRC, a CWST greater than about 53 dynes/cm is desirable. The CWST may typically be above from about 53 dynes/cm to about 115 dynes/cm, but the invention should not be limited thereby. A more preferable CWST is above about 60 dynes/cm, and a still more preferable CWST is from about 62 dynes/cm to less than about 90 dynes/cm.

If desired, the flow rate of biological fluid through the filter can be regulated to obtain a total flow period of about 10 to 40 minutes by selecting the appropriate element diameter, element thickness, fiber diameter, and density, and/or by varying the diameter of the tube either upstream or downstream of the filter, or both up and downstream. At these flow rates, leucocyte depletion efficiency in excess of 99.9% may be achieved. If PRP is the biological fluid being processed, these levels of efficiency may result in a PC product with less than about $0.1 \times 10^4$ leucocytes per unit of PC compared with the target of less than about $1 \times 10^4$.

The leucocyte depleting PRC porous medium is primarily intended for use with PRC obtained from donated blood within about 8 hours of the time the blood was drawn. It may also be used to filter PRC which has been stored at 4° C. for up to several weeks, but, since the risk of clogging during filtration increases with storage age, the risk can be reduced, by for example, using pre-filters preceding the media described herein.

A PRC porous medium of the invention can be made to have a wide range of efficiencies for leucocyte depletion. If the porous medium is composed of 2.6 μm fibers and weighs about $$\rho \left( 27.98 - \frac{29.26\,V}{100} \right) \text{ grams} \quad (3)$$

where
ρ=fiber density, grams/cc and V=voids volume, % then when used for leucocyte depletion of PRC, the log of the efficiency, defined as the ratio of the influent leucocyte concentration to the effluent leucocyte concentration, may be calculated from the formula $$\text{Log efficiency} = 25.5 \left( 1 - \frac{V}{100} \right) \quad (4)$$

In most applications, it is desirable to keep the time of flow of a unit of PRC through the porous medium when pressurized to about 30 to 300 mm of Hg to less than about 30 to 40 minutes; in order to achieve this flow rate, the device should preferably be configured to a flow area of about 30 to 60 cm².

For example, an 8.63 cm diameter (area=58.5 cm²) porous medium made using 7.7 grams of 2.6 μm diameter 1.38 g/cm³ density fiber with a voids volume of 76.5%, would meet the requirements of equation (3), and its leucocyte depletion efficiency, in accordance with equation (4) would be log 6. Thus, if the influent concentration were $10^9$ leucocytes/unit, then the effluent concentration would be $$10^9/10^6 = 10^3$$

Similarly, if made with V=88.2% using 2.6 μm diameter fibers of density 1.38 g/cc, the weight of the porous medium would be, per equation (3):

$$1.38 \left[ 27.98 - \left( 29.26 \times \frac{88.2}{100} \right) \right]$$
$$= 3.0 \text{ grams,}$$

and the log of the efficiency would be, per equation (4):

$$\text{Log efficiency} = 25.5 \left( 1 - \frac{88.2}{100} \right)$$
$$= 3.0$$

Thus, if the influent leucocyte concentration were $10^9$ per unit of PRC, the effluent concentration would be $$10^9/10^3 = 10^4 \text{ per unit}$$

Equations (3) and (4) are applicable to a voids volume range of about 73 to 88.5%, which spans the efficiency range from about log 3 to log 7.

Equations (3) and (4) provide very useful guidelines for designing and building optimal or near to optimal PRC filters with limited experimentation; however, a person familiar with the art will recognize that variations from these formulae and modifications to the porous media can be made to produce useful products. Exemplary modifications and their effect on the performance characteristics of the porous media are set out below:

| Desired Filter Characteristics | Changes from Equations (3) and (4) |
|---|---|
| Increased leucocyte depletion efficiency | Reduce fiber diameter[1] Increase weight of fiber Reduce voids volume |
| Decrease probability of clogging | Increase filter element area Provide prefiltration Increase voids volume |
| Decrease internal hold-up volume | Decrease voids volume[2] Eliminate prefiltration[2] Use finer fiber[1] |
| Increase flow rate of the PRC | Process the blood such that the PRC has lower hematocrit, hence lower viscosity Use higher head when filtering Increase filter area with concomitant reduction of thickness Increase filter element voids volume |
| Withstand higher applied differential pressure | Reduce element voids volume Use coarser fiber (at the cost of reduced efficiency) Use fiber with higher modulus |

(1) Use of too small a fiber diameter may result in collapse of the filter element at normal working differential pressure.
(2) May result in excessively long filtration times, or complete clogging prior to completion of a transfusion.

RED CELL BARRIER MEDIUM

Red cell barrier assemblies made in accordance with an embodiment of the invention and which are, for example, interposed between the blood collection bag and the PRP bag, will generally remove about 85% to 99% or more of the incident leucocytes, a removal rate that may not be sufficient to consistently achieve a residual leucocyte count of less than $10^4$ leucocytes per unit of PC. A principal function of this assembly, however, is to act as an automatic "valve" during the decantation process by instantly stopping the flow of a biological fluid such as the supernatant layer (e.g., PRP), at the moment that red cells contact the porous medium comprising porous media. The mechanism of this valve-like action is not well understood, but it may reflect aggregation of the red cells as they reach the porous surface, forming a barrier which prevents or blocks further flow of the supernatant layer through the porous medium.

Aggregation of red cells on contact with the porous filter appears to be related to the CWST and/or to other less well understood surface characteristics of the fibers which are generated by the herein described procedure for modifying the fibers. This theory for the proposed mechanism is supported by the existence of filters capable of highly efficient leucocyte depletion of human red blood cell suspensions and which have pore sizes as small as 0.5 μm, through which red cells pass freely and completely with no clogging, with applied pressure of the same magnitude as that used in the present invention.

On the other hand, the filters of the present invention, which typically have pore diameters larger than about 0.5 μm, abruptly stop the flow of red blood cells when the porous medium is contacted by the red cells. This suggests that the valve-like action is not related to or caused by pore size or by a filtration mechanism. The mechanism of this valve-like action is not well understood, but it may reflect zeta potential-related aggregation of the red cells as they reach the filter surface, forming a barrier which prevents or blocks further flow of a biological fluid containing red cells through the porous medium.

In one embodiment of the invention, the red cell filter assembly preferably includes a preferred range for the fiber surface area of about 0.04 to about 0.3 $M^2$, and, more preferably, about 0.06 to about 0.20 $M^2$. A preferred range for the porous medium flow area is about 3 to about 8 $cm^2$, and a more preferred range is about 4 to about 6 $cm^2$. A preferred range for the voids volume is about 71% to about 83%, and a more preferred range is from about 73% to about 80%. Because of its small size, a preferred device in accordance with this variation of the invention typically exhibits a low hold-up volume. For example, when the biological fluid processed is PRP, the device in accordance with this variation of the invention retains internally only about 0.5 to about 1 cc of PRP, representing less than a 0.5% loss of platelets.

In another variation of the devices of this invention, the PRP derived from a single unit of about 450 cc of human blood is passed, typically during a flow interval of about 10 to 40 minutes, through a filter comprising a porous medium, preferably comprising grafted fibers, with a surface area in the range of about 0.08 to about 1.0 square meters, and more preferably about 0.1 to about 0.7 square meters, with a voids volume in the range of about 50% to about 89%, and more preferably about 60% to about 85%. The filter element is preferably of right cylindrical form with the ratio of diameter to thickness preferably in the range of about 7:1 to about 40:1. The range of fiber diameter is preferred to be about 1.0 to about 4 μm and is more preferred to be in the range of about 2 to about 3 μm. In relation to the previous variation of the invention, this variation is made with higher fiber surface area, higher porous medium flow area, smaller porous medium density, and an increased voids volume.

All of these parameters can be varied; for example, the diameter of the porous medium could be reduced and the thickness increased while retaining the same total quantity of fiber, or the fibers could be larger in diameter while increasing the total quantity of fiber, or the fibers could be packed as opposed to preformed into a cylindrical disc. Such variations fall within the purview of this invention.

Another variation of this invention may comprise a porous medium wherein the upstream portion is of a higher density than the downstream portion. For example, the porous medium may comprise a higher density upstream layer for blocking the passage of red blood cells and a lower density downstream layer for the depletion of leucocytes.

In one embodiment of this invention, the fiber is surface modified in the same manner as in the preceding versions, but the fiber surface area element is increased while, at the same time, the density is somewhat reduced. In this way, the automatic blockage of flow on contact by red cells is combined with very high efficiency of leucocyte depletion.

A preferred range of fiber surface area for this variation of the invention is from about 0.3 to about 2.0 $M^2$, and a more preferred range is from about 0.35 to about 0.6 $M^2$. The upper limits of fiber surface area reflect the desire to accomplish the filtration in a relatively short time period, and may be increased if longer filtration times are acceptable. A preferred voids volume for the red cell barrier assembly is in the range of about 71% to about 83%, and more preferably about 75% to about 80%. A preferred flow area is from about 2.5 to about 10 $cm^2$, and a more preferred area is from about 3 to about 6 $cm^2$. Leucocyte depletion efficiencies in excess of about 99.9%, which corresponds to an average residual leucocyte content per unit of less than about $0.05\times10^4$, can be obtained.

In a preferred embodiment of the invention, a porous medium for use with a biological fluid such as a supernatant layer (e.g., PRP) may comprise the type of device disclosed in U.S. Pat. No. 4,880,548, herein incorporated by reference. In a preferred embodiment of the invention, a porous medium for use with a biological fluid such as a sediment layer (e.g., PRC), may comprise the type of device disclosed in U.S. Pat. No. 4,925,572 and U.S. Pat. No. 4,923,620, both incorporated herein by reference.

As noted above, as the sediment layer such as PRC is expressed from the collection bag, it may be processed through a device having a leucocyte depletion element in order to reduce the leucocyte content of the sediment layer. In accordance with the invention, the porous medium for removing leucocytes from the packed red cell component of a biological fluid comprises a leucocyte removal element or porous medium. The preferred element is typically made using radiation grafted melt blown fibers having an average diameter of from about 1 to about 4 μm, preferably from about 2 to about 3 μm. Polybutylene terephthalate (PBT) web, which is a preferred material, may be hot compressed to a voids volume of about 65% to about 90% and preferably to about 73% to about 88.5%.

SEPARATION ASSEMBLY

The present invention involves the separation of one or more components from a biological fluid. In accordance with the present invention, a biological fluid, particularly blood, may be exposed to a separation medium suitable for passing at least one component of the biological fluid, particularly plasma, therethrough, but not other components of the biological fluid, particularly platelets and/or red cells. Clogging of the separation medium by these other components is minimized or prevented.

In the embodiment of the invention which includes a separation assembly 14, preferably a non-centrifugal separation device, the supernatant layer (e.g., PRP) may be passed through a leucocyte depletion assembly, and then passed through the non-centrifugal separation device 14, where it may be processed and separated into components, which may be separately collected in container 15 and container 16. In a preferred embodiment, if the supernatant fluid is PRP, it may be separated into plasma and platelet concentrate as the PRP passes through the non-centrifugal separation device.

Figure 5:
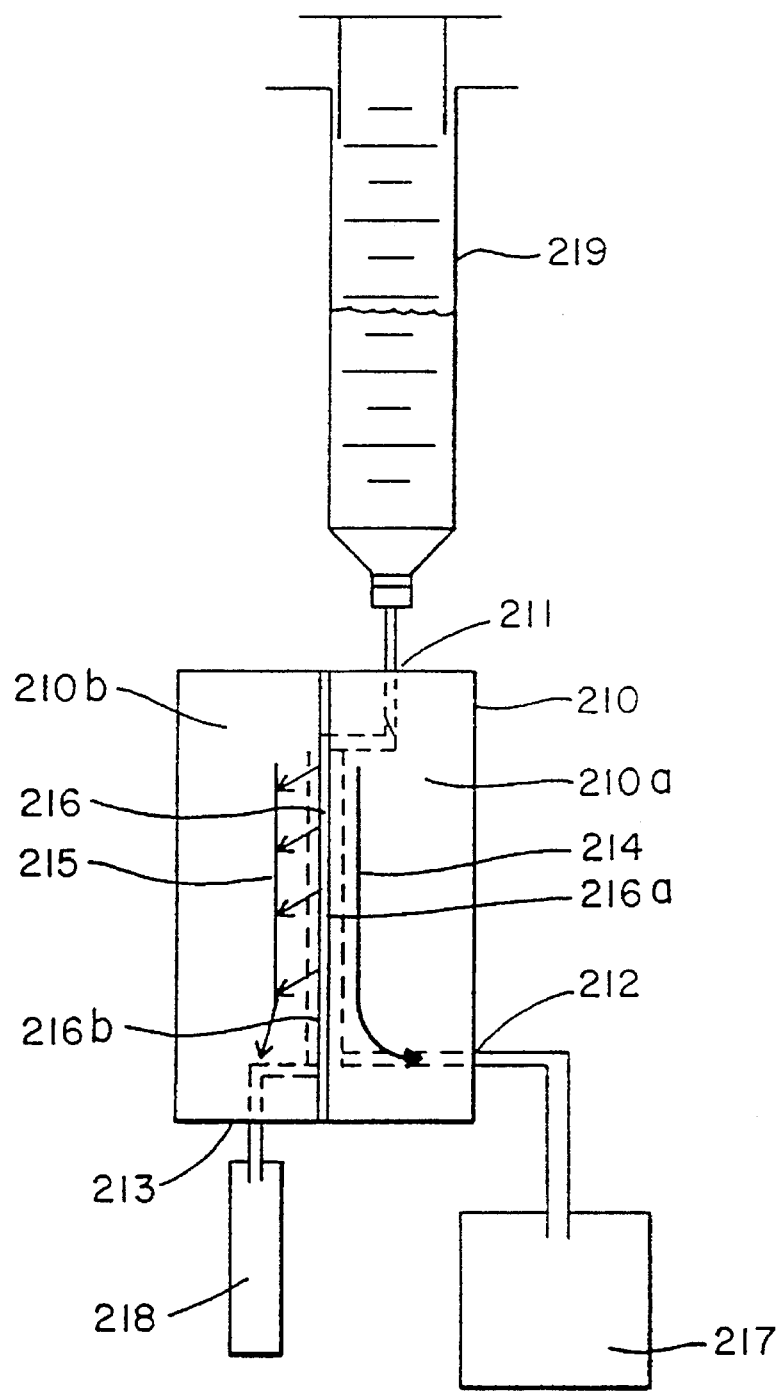
FIG. 5 is an elevation of an embodiment of the present invention.

As shown in FIG. 5, a preferred separation device of the present invention comprises a housing 210 having first and second portions 210a, 210b joined in any convenient manner. For example, the first and second housing portions 210a, 210b may be joined by means of an adhesive, a solvent, or one or more connectors. The housing 210 also has an inlet 211 and first and second outlets 212 and 213, respectively, such that a first fluid flow path 214 is established between the inlet 211 and first outlet 212 and a second fluid flow path 215 is established between the inlet 11 and the second outlet 13. A separation medium 216 having first and second surfaces 216a, 216b is positioned inside the housing 210 between the first and second housing portions 210a, 210b. Further, the separation medium 216 is positioned parallel to the first fluid flow path 214 and across the second fluid flow path 215.

Embodiments of the present invention may be configured in a variety of ways to ensure maximum contact of the biological fluid with the first surface 216a of separation medium 216 and to reduce or eliminate clogging on the first surface 216a of the separation medium. For example, the separation device may include a first shallow chamber facing the first surface 216a of the separation medium 216. The first chamber may include an arrangement of ribs which spread the flow of biological fluid over the entire first surface 216a of the separation medium 216. Alternatively, the first chamber may include one or more channels, grooves, conduits, passages, or the like which may be serpentine, parallel, curved, or a variety of other configurations.

The fluid flow channels may be of any suitable design and construction. For example, the channels may have a rectangular, triangular, or semi-circular cross section and a constant depth. Preferably, the channels have a rectangular cross section and vary in depth, for example, between inlet 211 and outlet 212.

Figure 6:
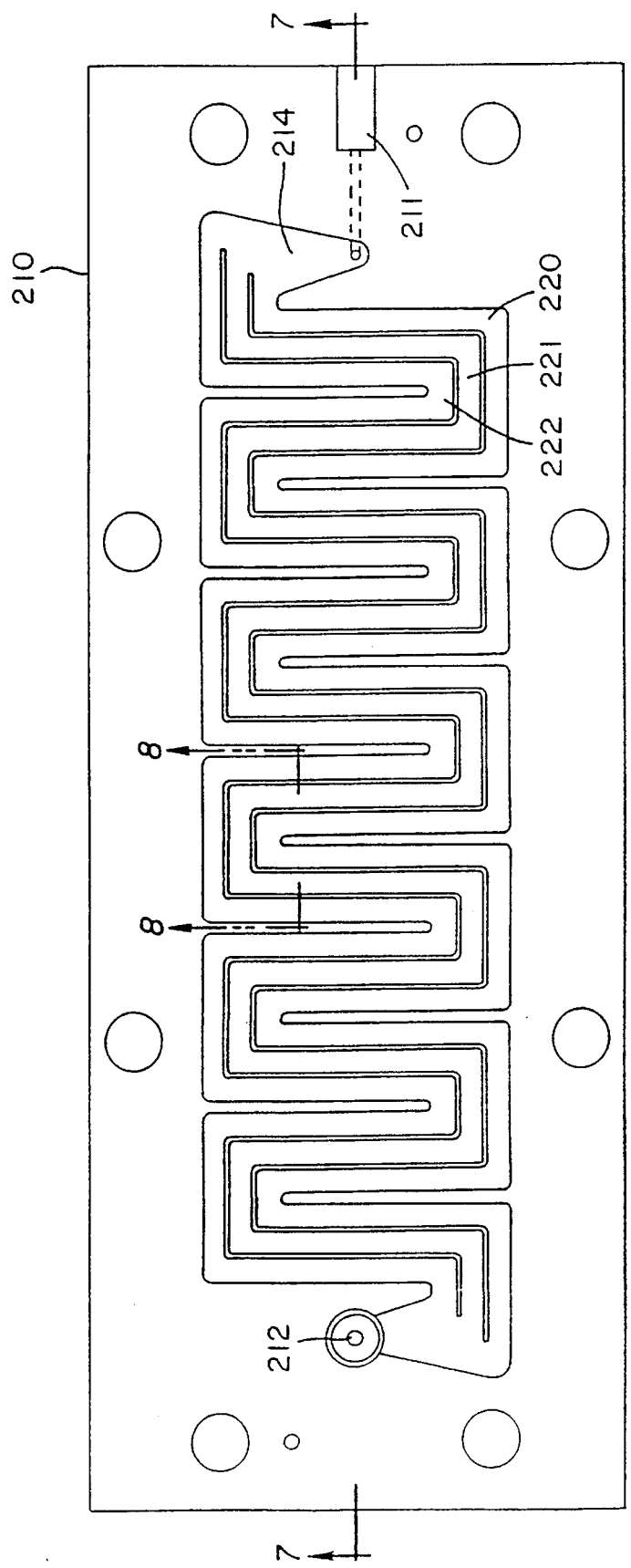
FIG. 6 is a cross-section of an embodiment of the invention, showing the first fluid flow path in a separation device according to the invention.
Figure 8:
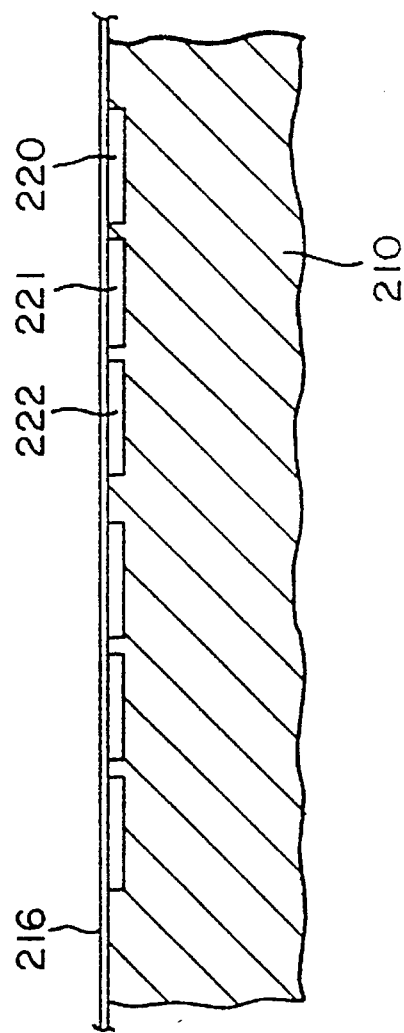
FIG. 8 is a section of FIG. 6, along B—B.
Figure 7:
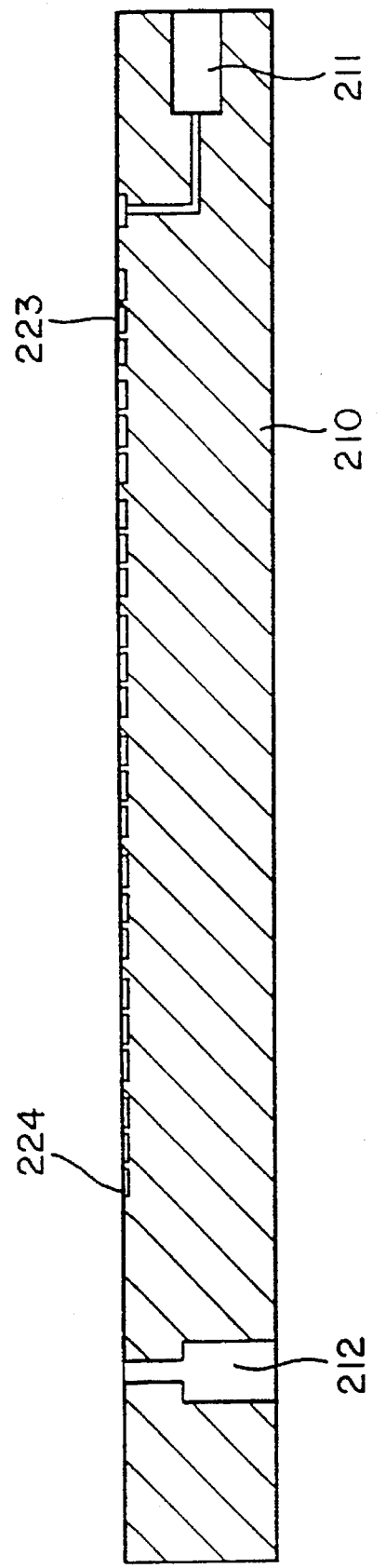
FIG. 7 is a section of FIG. 6, along A—A.

In the embodiment shown in FIGS. 6, 7, and 8, the inlet 211 of the housing 210 is connected to serpentine fluid flow channels 220, 221, and 222 which face the first surface 216a of the separation medium 216. These channels 220–222 separate the inlet flow of biological fluid into separate flow paths tangential to the first surface 216a of the separation medium 216. Extending along the first surface 216a, the serpentine fluid flow channels 220, 221, and 222 may be recombined at first outlet 212 of the housing 210.

Embodiments of the present invention may also be configured in a variety of ways to minimize back pressure across the separation medium 216 and to ensure a sufficiently high velocity of flow to the second outlet 212 to prevent fouling of surface 216a, while minimizing hold-up volume. The separation device includes a second shallow chamber facing the second surface 216b of the separation medium 216. Like the first chamber, the second chamber may include an arrangement of ribs or may comprise one or more channels, grooves, conduits, passages, or the like which may be serpentine, parallel, curved, or have a variety of other configurations.

Figure 11:
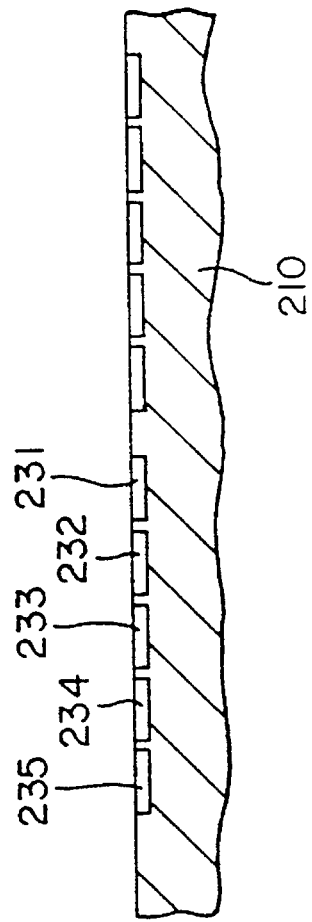
FIG. 11 is a section of FIG. 9, along D—D.

The fluid flow channels may be of any suitable design and construction. For example, the channels may have a rectangular, semi-circular, or triangular cross section and a constant or variable depth. In the embodiment shown in FIGS. 9–11, several serpentine fluid flow channels 231, 232, 233, 234, and 235 face the second surface 216b of the separation medium 216. Extending along the second surface 216b, the serpentine fluid flow channels 231–235 may be recombined at the second outlet 213.

Ribs, walls, or projections 241, 242 may be used to define the channels 220–222, 231–235 of the first and second chambers and/or may support or position the separation medium 216 within the housing 210. In a preferred embodiment of the invention, there are more walls 242 in the second chamber than in the first chamber to prevent deformation of the separation medium 216 caused by pressure differential through the separation medium.

In use, a biological fluid, e.g., whole blood or PRP, is fed under sufficient pressure into the inlet 211 of housing 210 from any suitable source of the biological fluid. For example, the biological fluid may be injected from a syringe into the inlet 211 or it may be forced into the inlet 211 from a flexible bag using a gravity head, a pressure cuff, or an expressor. From the inlet 211, the biological fluid enters the channels 220–222 of the first chamber and passes tangentially or parallel to the first surface 216a of the separation medium 216 on the way to the first outlet 212 via the first fluid flow path 214. At least one component of the biological fluid, e.g., plasma, passes through the separation medium 216, enters the channels 231–235 of the second chamber, and is directed toward the second outlet 213 via the second fluid flow path 215. As the biological fluid continues along the first flow path 214 tangentially or parallel to the first surface 216a of the separation medium 216, more and more plasma crosses the separation medium 216. A plasma-depleted fluid then exits the housing 210 at the first outlet 212 and is recovered in one container 217 while plasma exits the housing 210 at the second outlet 213 and is recovered in another container 218.

While any biological fluid containing plasma may be used in conjunction with the present invention, the present invention is particularly well-suited for use with blood and blood products, especially whole blood or PRP. By subjecting PRP to processing in accordance with the present invention, PC and platelet-free plasma may be obtained without centrifugation of the PRP and the attendant disadvantages discussed above. Likewise, platelet-free plasma may be obtained from whole blood. The biological fluid may be supplied in any suitable quantity consistent with the capacity of the overall device and by any suitable means, e.g., in a batch operation by, for example, a blood bag connected to an expressor or a syringe, or in a continuous operation as part of, for example, an apheresis system. Exemplary sources of biological fluid include a syringe 219, as shown in FIG. 5, or a biological fluid collection and processing system such as that disclosed in U.S. Ser. No. 07/609,654, filed Nov. 6, 1990, incorporated herein by reference. A source of biological fluid may also include an apheresis system, and/or may include a system in which biological fluid is recirculated through the system.

The separation medium and housing may be of any suitable material and configuration and the separation medium may be arranged in the present inventive device in any suitable manner so long as the biological fluid flow tangential or parallel to the separation medium is maintained to a sufficient extent to avoid or minimize substantial platelet adhesion to the separation membrane. The hydrodynamics of flow parallel to a surface are indeed believed to be such that during flow parallel to the surface, platelets develop a spin which causes them to be recovered from the surface. While the preferred device has one inlet and two outlets, other configurations can be employed without adversely affecting the proper functioning of the device. For example, multiple inlets for a biological fluid may be used so long as the biological fluid flows tangentially across the face of the separation medium. The plasma may preferably be stored in a region separated from the separation medium in order to avoid possible reverse flow of the plasma back across the separation medium to the plasma-depleted fluid.

One skilled in the art will recognize that platelet adhesion may be controlled or affected by manipulating any of a number of factors: velocity of the fluid flow, configuration of the channel, depth of the channel, varying the depth of the channel, the surface characteristics of the separation medium, the smoothness of the medium's surface, and/or the angle at which the fluid flow crosses the face of the separation medium, among other factors. For example, the velocity of the first fluid flow is preferably sufficient to remove platelets from the surface of the separation medium. Without intending to be limited thereby, a velocity in excess of about 30 cm/second has been shown to be adequate.

The velocity of the fluid flow may also be affected by the volume of the biological fluid, by varying the channel depth, and by the channel width. For example, the channel depth may be varied from about 0.25 inch to about 0.001 inch, as shown in FIG. 7. One skilled in the art will recognize that a desired velocity may be achieved by manipulating these and other elements. Also, platelets may not adhere as readily to a separation medium having a smooth surface as compared to a membrane having a rougher surface.

In accordance with the invention, the separation medium comprises a porous medium suitable for passing plasma therethrough. The separation medium, as used herein, may include but is not limited to polymeric fibers (including hollow fibers), polymeric fiber matrices, polymeric membranes, and solid porous media. Separation media according to the invention remove plasma from a biological solution containing platelets, typically whole blood or PRP, without removing proteinaceous blood components and without allowing a substantial amount of platelets to pass therethrough.

A separation medium, in accordance with the invention, preferably exhibits an average pore rating generally or intrinsically smaller than the average size of platelets, and, preferably, platelets do not adhere to the surface of the separation medium, thus reducing pore blockage. The separation medium should also have a low affinity for proteinaceous components in the biological fluid such as PRP. This enhances the likelihood that the platelet-poor solution, e.g., platelet-free plasma will exhibit a normal concentration of proteinaceous clotting factors, growth factors, and other needed components.

For the separation of about one unit of whole blood, a typical separation device according to the invention may include an effective pore size smaller than platelets on the average, typically less than about 4 micrometers, preferably less than about 2 micrometers. The permeability and size of the separation device is preferably sufficient to produce about 160 cc to about 240 cc of plasma at reasonable pressures (e.g., less than about 20 psi) in a reasonable amount of time (e.g., less than about one hour). In accordance with the invention, all of these typical parameters may be varied to achieve a desired result, i.e., varied preferably to minimize platelet loss and to maximize platelet-free plasma projuction.

In accordance with the invention, a separation medium formed of fibers may be continuous, staple, or melt-blown. The fibers may be made from any material compatible with a biological fluid containing platelets, e.g., whole blood or PRP, and may be treated in a variety of ways to make the medium more effective. Also, the fibers may be bonded, fused, or otherwise fixed to one another, or they may simply be mechanically entwined. A separation medium formed of a membrane, as the term is used herein, refers to one or more porous polymeric sheets, such as a woven or non-woven web of fibers, with or without a flexible porous substrate, or may comprise a membrane formed from a polymer solution in a solvent by precipitation of a polymer when the polymer solution is contacted by a solvent in which the polymer is not soluble. The porous, polymeric sheet will typically have a substantially uniform, continuous matrix structure containing a myriad of small largely interconnected pores.

The separation medium of this invention may be formed, for example, from any synthetic polymer capable of forming fibers or a membrane. While not necessary to the apparatus or method of the invention, in a preferred embodiment the polymer is capable of serving as a substrate for grafting with ethylenically unsaturated monomeric materials. Preferably, the polymer should be capable of reacting with at least one ethylenically unsaturated monomer under the influence of ionizing radiation or other activation means without the matrix being adversely affected. Suitable polymers for use as the substrate include, but are not limited to, polyolefins, polyesters, polyamides, polysulfones, polyarylene oxides and sulfides, and polymers and copolymers made from halogenated olefins and unsaturated nitriles. Preferred polymers are polyolefins, polyesters, and polyamides, e.g., polybutylene terephthalate (PBT) and nylon. In a preferred embodiment, a polymeric membrane may be formed from a fluorinated polymer such as polyvinylidene difluoride (PVDF). The most preferred separation media are a microporous polyamide membrane or a polycarbonate membrane.

Surface characteristics of a fiber or membrane can be affected as noted above for a porous medium. An exemplary radiation gratting technique employs at least one of a variety of monomers each comprising an ethylene or acrylic moiety and a second group, which can be selected from hydrophilic groups (e.g., —COOH, or —OH) or hydrophobic groups (e.g., c methyl group or saturated chains such as —$CH_2CH_2CH_3$). Grafting of the fiber or membrane surface may also be accomplished by compounds containing an ethylenically unsaturated group, such as an acrylic moiety, combined with a hydroxyl group, such as, hydroxyethyl methacrylate (HEMA). Use of HEMA as the monomer contributes to a very high CWST. Analogues with similar characteristics may also be used to modify the surface characteristics of fibers.

In accordance with an embodiment of the invention, the separating medium may be surface-modified, typically by radiation grafting, in order to achieve the desired performance characteristics, whereby platelets are concentrated with a minimum of medium blocking, and whereby the resulting plasma solution contains essentially all of its native proteinaceous constituents. Exemplary membranes having a low affinity for proteinaceous substances are disclosed in U.S. Pat. Nos. 4,886,836; 4,906,374; 4,964,989; and 4,968,533, all incorporated herein by reference.

Suitable membranes in accordance with an embodiment of the invention may be microporous membranes and may be produced by a solution casting method.

As noted above, establishing a tangential flow of the biological fluid being processed parallel with or tangential to the face of the separation medium minimizes platelet collection within or passage through the separation medium. In accordance with the invention, the tangential flow can be induced by any mechanical configuration of the flow path which induces a high local fluid velocity at the immediate membrane surface. The pressure driving the biological fluid across the separation medium may be derived by any suitable means, for example, by gravity head or by an expressor.

The tangential flow of the biological fluid may be directed tangential or parallel to the face of the separation medium in any suitable manner, preferably utilizing a substantial portion of the separation medium surface while maintaining a sufficient flow to ensure that the platelets do not clog or block the pores of the separation medium. The flow of the biological fluid is preferably directed tangentially or parallel to the face of the separation medium through use of at least one serpentine fluid flow channel which is designed to maximize utilization of the separation medium, ensure a sufficiently total area contact between the biological fluid and the separation medium, and maintain a sufficient flow of biological fluid to minimize or prevent platelet adhesion to the separation medium. Most preferably, several (e.g., three or more) fluid flow channels are utilized so as to fix the separation medium in place and to prevent sagging of the membrane due to the applied pressure. The fluid flow channels may be of any suitable design and construction and preferably are variable with respect to depth such as depth to maintain optimal pressure and fluid flow across the face of the separation medium. Fluid flow channels may also be utilized on the side of the separation medium opposite the biological fluid tangential flow to control the flow rate and pressure drop of a platelet-poor fluid, such as plasma.

The present inventive device may similarly be part of an apheresis system. The biological fluid to be processed, the platelet-rich solution, and/or the platelet-poor solution may be handled in either a batch or continuous manner. The sizes, nature, and configuration of the present inventive device can be adjusted to vary the capacity of the device to suit its intended environment.

GAS INLET/OUTLET

Under certain circumstances, it may be desirable to maximize the recovery of a biological fluid retained or entrapped in various elements of the biological fluid processing system. For example, under typical conditions, using a typical device, the biological fluid will drain through the system until the flow is stopped, leaving some of the fluid in the system. In one embodiment of the invention, the retained fluid may be recovered by using at least one gas inlet and/or at least one gas outlet. An exemplary configuration of this embodiment is shown in FIG. 3.

The gas outlet is a porous medium which allows gas that may be present in a biological fluid processing system when the biological fluid is processed in the system, out of the system. The gas inlet is a porous medium which allows gas into a biological fluid processing system.

As used herein, gas refers to any gaseous fluid, such as air, sterilized air, oxygen, carbon dioxide, and the like; it is intended that the invention is not to be limited to the type of gas used.

The gas inlet and gas outlet are chosen so that the sterility of the system is not compromised. The gas inlet and the gas outlet are particularly suited for use in closed systems, or may be used later, for example, within about 24 hours of a system being opened.

The gas inlet and the gas outlet each comprise at least one porous medium designed to allow gas to pass therethrough. A variety of materials may be used, provided the requisite properties of the particular porous medium are achieved. These include the necessary strength to handle the differential pressures encountered in use and the ability to provide the desired filtration capability while providing the desired permeability without the application of excessive pressure. In a sterile system, the porous medium should also preferably have a pore rating of about 0.2 micrometer or less to preclude bacteria passage.

The gas inlet and gas outlet may comprise a porous medium, for example, a porous fibrous medium, such as a depth filter, or a porous membrane or sheet. Multilayered porous media may be used, for example, a multilayered microporous membrane with one layer being liquophobic and the other liquophilic.

Preferred starting materials are synthetic polymers including polyamides, polyesters, polyolefins, particularly polypropylene and polymethylpentene, perfluorinated polyolefins, such as polytetrafluoroethylene, polysulfones, polyvinylidene difluoride, polyacrylonitrile and the like, and compatible mixtures of polymers. The most preferred polymer is polyvinylidene difluoride. Within the class of polyamides, the preferred polymers include polyhexamethylene adipamide, poly-$\epsilon$-caprolactam, polymethylene sebacamide, poly-7-aminoheptanoamide, polytetramethylene adipamide (nylon 46), or polyhexamethylene azeleamide, with polyhexamethylene adipamide (nylon 66) being most preferred. Particularly preferred are skinless, substantially alcohol-insoluble, hydrophilic polyamide membranes, such as those described in U.S. Pat. No. 4,340,479.

Other starting materials may also be used to form the porous media of this invention including cellulosic derivatives, such as cellulose acetate, cellulose propionate, cellulose acetate-propionate, cellulose acetate-butyrate, and cellulose butyrate. Non-resinous materials, such as glass fibers, may also be used.

The rate of air flow through the gas outlet or the gas inlet can be tailored to the specific biological fluid or fluids of interest. The rate of air flow varies directly with the area of the porous medium and the applied pressure. Generally, the area of the porous medium is designed to enable the biological fluid processing system to be primed in a required time under the conditions of use. For example, in medical applications it is desirable to be able to prime an intravenous set in from about 30 to about 60 seconds. In such applications as well as in other medical applications, the typical porous medium is a membrane, which may be in the form of a disc which has a diameter from about 1 mm to about 100 mm, preferably from about 2 mm to about 80 mm, and more preferably from about 3 mm to about 25 mm.

In accordance with the invention, the processing system may be provided with a gas inlet to permit the introduction of gas into the system, and/or with a gas outlet to permit gases in the various elements of the system to be separated from the biological fluid to be processed. The gas inlet and the gas outlet may be used together in connection with at least one assembly, porous medium, or container in the system, or they may be used separated.

To that end, a gas inlet or gas outlet may be included in any of the various elements of the biological fluid processing system. By way of illustration, a gas inlet or gas outlet may be included in at least one of the conduits which connect the different containers, in a wall of the containers that receive the processed biological fluid, or in a port on or in one of those containers. The gas inlet or gas outlet may also be included on or in a combination of the elements mentioned above. Also, an assembly or porous medium may include one or more gas inlet or gas outlet as described above. Generally, however, it is preferred to include a gas inlet or gas outlet in the conduits which connect the containers or in the functional medical device. Included within the scope of the invention is the use of more than one gas inlet or gas outlet in any conduit, receiving container, assembly, or porous medium.

It will be apparent to one skilled in the art that the placement of a gas inlet or a gas outlet may be optimized to achieve a desired result. For example, it may be desirable to locate the gas inlet upstream of a porous medium and in or as close to the first container as is practical in order to maximize the recovery of biological fluid. Also, it may be desirable to locate the gas outlet downstream of the porous medium and as close to the receiving container as is possible in order to maximize the volume of gas that is removed from the system.

Such placement of the gas inlet or gas outlet is particularly desirable where there is only one gas inlet or gas outlet in the system.

In accordance with the invention, recovery from the various elements of the biological fluid processing system may be maximized. For example, whole blood is subjected to a processing step, resulting in separate PRP and PRC layers. Then, the separate fractions of blood components are expressed to their respective receiving containers through the appropriate conduits and porous media, if any. Blood product that has become entrapped in these elements during processing may be recovered either by passing purge gas through the conduits and porous media, or by creating at least a partial vacuum in the system to draw out the retained blood product and to permit it to drain into the appropriate receiving container or assembly.

The purge gas may be from any of a number of sources. For example, the biological fluid processing system may be provided with a storage container for the storage of the purge gas, the purge gas may be the gas that was removed from the system during the processing function, or the purge gas may be injected aseptically into the system from an outside source (e.g., through a syringe). For example, it may be desirable to use sterile purge gas that has been sterilized in a separate container apart from the biological fluid processing system.

In accordance with the invention, a clamp, closure, or the like may be positioned on or in any or all of the conduits in order to facilitate a desired function, i.e., establishing a desired flow path for biological fluid or gas. For example, when processing a biological fluid (e.g., PRP) through a system such as is illustrated in FIG. 3, during the removal of gases from the conduits and the leucocyte depletion assembly, it may be desirable to clamp the conduit immediately below gas outlet 54. When it is desirable to use the gas inlet 53 to maximize the recovery of a biological fluid, the clamp below gas outlet 54 is released, and a clamp in the conduit adjacent to gas intake 53 is opened. As exemplified in FIG. 3, other gas inlets and gas outlets (e.g., 51 and 52) may be operated in a similar manner.

With continued reference to FIG. 3, as a column of biological fluid (e.g., PRP) flows from the first container 11 through the conduit and the leucocyte depletion assembly 13, towards the satellite bag 41, it drives the gas in those elements towards the gas outlet 54.

The gas outlet may comprise a branching element with three legs. One leg may include a liquophobic porous medium which preferably has a pore size of not greater than 0.2 μ. At the branching element, gas ahead of the column of biological fluid moves into one leg of the branching element. Since the gas passes through the liquophobic porous medium, but the biological fluid does not, the gas is separated from the PRP and is precluded from entering the satellite bag 15.

The gases separated by the gas outlet 54 may be vented from the system, or they may be collected in a gas container (not shown) and returned to the system as a purge gas to facilitate the recovery of biological fluid that becomes trapped in the various components of the system.

After the system is primed and the gas outlet is inactivated, the clamp adjacent to the containers or assembly is opened to allow the containers to fill with processed biological fluid. This continues until the collection bag 11 collapses. In order to recover the very valuable biological fluid retained in the system, ambient air or a sterile gas may enter the system through gas inlet 51 or 53. If gas inlet 51 or 53 is a manual inlet means, a closure is opened or a clamp released; if the gas inlet 51 or 53 is automatic, the pressure differential between the gas inlet and the containers will cause the air or gas to flow through the conduits, through the porous media, and towards the respective containers. In the process, retained biological fluid that is trapped in those elements during processing are recovered from those components and collected in the containers. It should be noted that the purge air or gas is preferably separated from the biological fluid at gas outlet 52 or 54, so that little, if any, purge gas will be received by the containers. This may be accomplished by clamping the conduit downstream of the gas outlet 52 or 54. In another embodiment of the invention, the purge air or gas may be separated from the system through a gas outlet located in the bag itself.

BRACKET

In another embodiment, the invention also includes a bracket which secures a filter assembly comprising a porous medium or one or more components of an assembly in place during centrifugation so that it (they) is (are) not damaged by the stresses generated during centrifugation.

The blood collection and processing assembly 10, with one or more satellite bags attached or connected via a conduit, may be used integrally to separate components from whole blood. This embodiment of the invention will be better understood by reference to the exemplary configuration shown in FIG. 4. During the centrifugation step in which the red cells are concentrated at the bottom of the collection bag, forces of up to about 5000 times gravity (5000 G) or more may be generated. Therefore, the collection bag is preferably flexible, as are the other bags, allowing them to settle to the bottom and against the walls of a centrifuge bucket 120, so that the bags themselves are subject to little or no stress.

In contrast to the flexibility and pliability of the bags and tubing, the porous medium is typically contained in a rigid plastic housing (the combination of which is termed a filter assembly). The PRC housing is typically of larger dimensions than the PRP housing, and is therefore subject to an increased probability of suffering or causing damage during centrifugation. For example, a typical PRC filter assembly may weigh about 20 grams (about 0.04 lbs), but its effective weight may be 5000 times greater, or about 200 lbs, under centrifugation conditions of 5000 G. In conventional centrifugation systems it is therefore difficult to avoid shattering the plastic housing. Even careful placement of the PRC filter assembly in the centrifuge bucket is likely to result in damage to the plastic tubing or to the bags. Furthermore, it is undesirable to enlarge the centrifuge bucket to accommodate the filter assembly in the bucket during the centrifugation step, as this would not only require the use of a larger and more costly centrifuge, but it would also require retraining the thousands of blood processing technicians to expertly assemble the blood bag sets into a new type of centrifuge bucket.

Accordingly, it is desirable that an improved blood collection and processing system or set should be usable with existing centrifuge buckets. In accordance with the invention, this is preferably accomplished by locating the PRC filter assembly away from the greatest amount of G force; this is more preferably outside or partly outside of the conventionally used centrifuge bucket, in the manner shown in FIG. 4.

Figure 4:
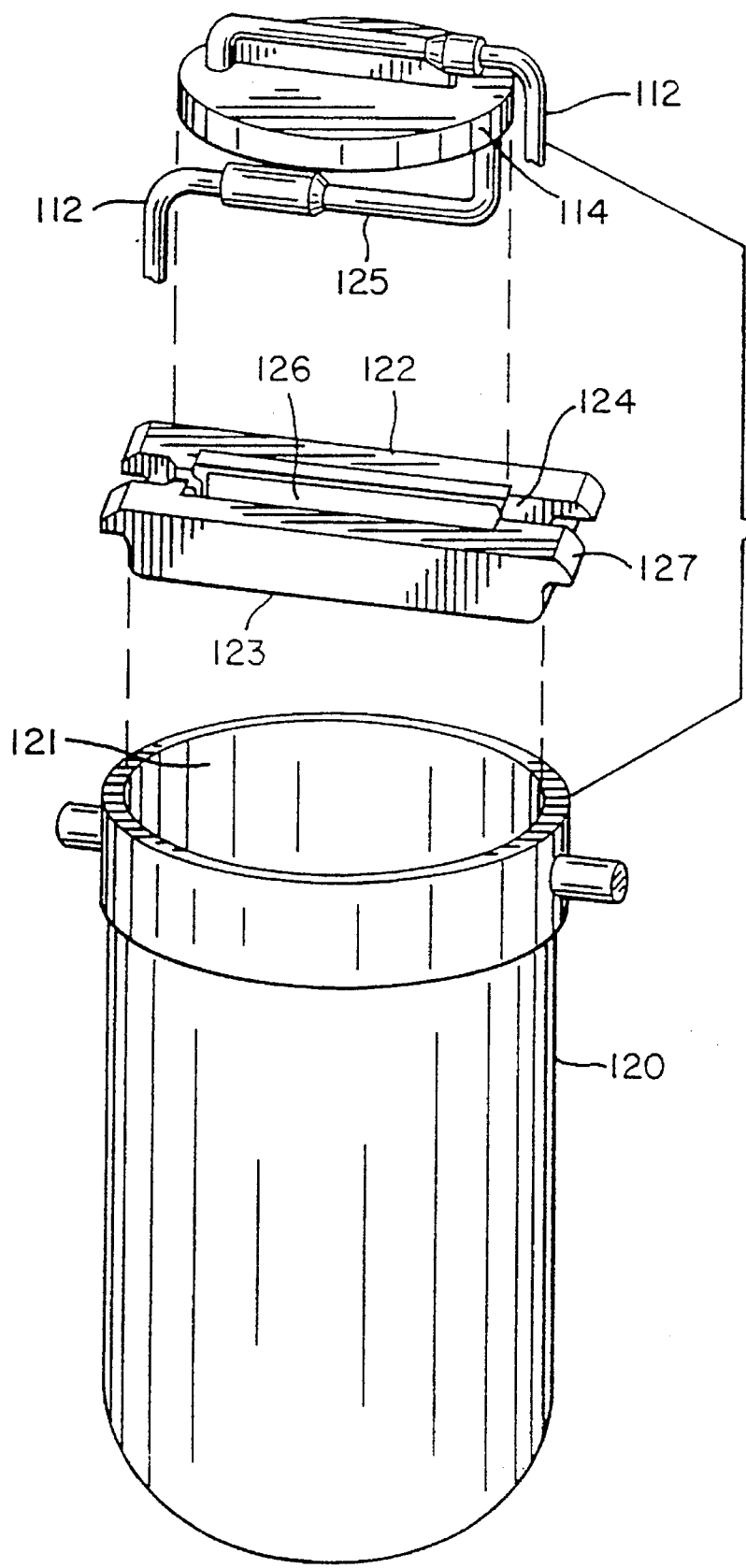
FIG. 4 is an exploded perspective view of one embodiment of a filter assembly, a centrifuge bucket, and a holder to properly position the filter assembly on the bucket.

In FIG. 4 the bucket 120 depicts a centrifuge bucket such as is used in current blood bank practice. These buckets are typically constructed with heavy walls of high strength steel which enclose open space 121 into which the blood bag, its satellite bags, and the interposed tubing may be placed. The bracket 122 used to hold a filter assembly may be made of any high strength material, preferably metal or metallic alloy; titanium or stainless steel are more preferred for their strength and the ease with which sanitary conditions can be maintained. The lower portion 123 of bracket 122 is configured to cooperatively fit into cavity 121, preferably at a depth of about 0.5 to about 1 cm. Spring clips or other means may be used to position and/or retain bracket 122 in the bucket 120. Groove 124 located in the upper portion of bracket 122, is preferably configured to cooperatively accept the outlet port 125 of the filter assembly 114, and to allow the bottom portion surfaces of bracket 122 adjacent to groove 124. The surface of bracket 122 adjacent to groove 124. The central portion 126 of groove 124 may be proportioned such that port 125 at the filter assembly 114 fits into at least a portion of the groove 124 with a friction fit. The ends of groove 124 are preferably reduced to a width such that flexible tubing 112 connected to the inlet and outlet of the filter assembly 114 is firmly retained, thereby helping to stabilize the filter assembly 114 when positioned onto bracket 122. The unsupported portions of flexible tubing 112 then drop into the bucket in communication with the balance of the blood collection set contained therein. It is preferred that the bracket 122 retain the filter assembly 114 so that the plane of the porous medium is substantially perpendicular to the G force created during operation of the centrifuge. Also, the bracket and filter assembly should be positioned on or in the centrifuge bucket without interfering with the normal free-swinging action of the bucket 120 in the centrifuge during rotation.

Because the PRP filter is typically relatively small and very light, it may be positioned within the bucket with the bags and the tubing. In another embodiment of the invention, however, the groove 124 may be configured to hold more than one filter assembly, for example, both a PRC and a PRP filter assembly.

In another embodiment of the invention, a larger bracket may be employed to hold a first filter assembly and a second bracket holding a second filter assembly may be nested on top of the first bracket and filter assembly. One skilled in the art will recognize that various designs, configurations, and/ or means may be employed to accomplish these functions.

Another feature of the invention is the location and manner in which the porous medium, particularly the PRC medium, is mounted on the centrifuge bucket during the centrifugation operation. Trials of a number of test filter housings designed to fit within the centrifuge bucket convincingly demonstrated that perforation of tubing lines by the housing is a frequent occurrence during centrifugation. Also, it is very difficult to design a housing that can reliably withstand d without shattering. Further, the existing centrifuge buckets are designed to carry the conventional blood collection sets, which incorporate no filter elements. Fitting the added bulk of a PRC filter assembly into a conventional bucket was, thus, very difficult. These very serious problems were eliminated by mounting the PRC filter assembly on a bracket outside of the bucket. This provides adequate support for the filter assembly by cooperatively arranging flange portion 127 of bracket 122 (FIG. 4) to accommodate the contours of the centrifuge bucket. Furthermore, bracket 122 is preferably positioned above the top of the bucket, a location which is much closer to the center of rotation of the centrifuge that the force to which the filter assembly is subjected is about 40% to about 60% that of the bottom of the bucket 120. Additionally, the narrow slots at each end of the bracket hold the tubing connections firmly, and permit the tubes to drop back into the bowl. Surprisingly, the suspended portions of the tubing tolerate the centrifuging operation very well.

A system according to the present invention may be used in conjunction with other assemblies or porous media, including filtration and/or separation devices, e.g., a device for removing leucocytes from a platelet-containing solution or concentrate. Exemplary devices are disclosed in U.S. Pat. No. 4,880,548, and U.S. Pat. No. 4,925,572 incorporated herein by reference in their entirety.

Housings can be fabricated from any suitably impervious material, including an impervious thermoplastic material. For example, the housing may preferably be fabricated by injection molding from a transparent or translucent polymer, such as an acrylic, polystyrene, or polycarbonate resin. Not only is such a housing easily and economically fabricated, but it also allows observation of the passage of the fluid through the housing.

The housing into which the porous medium is sealed or interference fit is designed to achieve convenience of use, rapid priming, and efficient air clearance.

While the housing may be fashioned in a variety of configurations, the housing of a porous medium according to the present invention preferably comprises a housing such as that disclosed in U.S. Pat. Nos. 4,880,548; 4,923,620; and 4,925,572, which are generally similar in configuration to housing 114 in FIG. 4.

A number of additional containers may be in communication with the biological fluid processing system, and can be utilized to define different flow paths. For example, an additional satellite bag containing physiological solution may be placed in communication with the biological fluid processing system upstream of the leucocyte depletion assembly (e.g., through the gas inlet), and the solution may be passed through the leucocyte depletion assembly so that the biological fluid that was held up in the assembly can be collected.

Similarly, a satellite bag containing physiological solution may be placed in communication with the biological fluid processing system downstream of the leucocyte depletion assembly (e.g., through the gas outlet), and the solution may be passed through the leucocyte depletion assembly so that the biological fluid that was held up in the assembly can be later collected.

It will be appreciated that when the biological fluid from the collection bag 11 is expressed towards the containers, some of the biological fluid may be trapped in the conduits and/or the porous mediums. For example, 8 cc to 35 cc is typically retained in the system; but as little as 2 cc to as much as 150 cc or more may be retained in some types of systems.

In an embodiment of the invention (not shown), air or gas may be stored in at least one gas container; upon opening of valve or clamp means in the conduits, gas can be fed through them to purge the conduits and assemblies, thereby facilitating the recovery of biological fluid that may have been trapped during processing.

Preferably, the purge air or gas is fed to the conduits at a point as close as is reasonably possible to container 11 to maximize the volume of biological fluid recovered. The air or gas container is preferably flexible so that the gas therein may be fed to the system merely by simple compression. The biological fluid containers and the air or gas containers may be composed of the same material.

Priming, as used herein, refers to wetting or priming the inner surfaces of a device or assembly prior to its actual use allowing a separate assembly to be injected into the system. A valve or clamp is opened to allow fluid to flow through the assembly; then, with the passage of fluid through the assembly, gas downstream of the fluid is expelled through the gas outlet until fluid reaches a branching element, at which point the clamp is closed. With the clamp in a closed position, the connector downstream of the gas outlet may be opened or readied for use without fluid in the assembly dripping through the connector.

In accordance with the invention, the biological fluid collection and processing assembly should be able to withstand rigorous sterilization and centrifugation environments, typically consisting of radiation sterilization (at about 2.5 megarads), and/or autoclaving (at about 110° C. to about 120° C. for about 15 to 60 minutes), and/or centrifugation (typically about 2500 to 3500 G for about 5 to 15 minutes; however, depending on which biological fluid component is intended to have maximum recovery, the centrifugation may be about 5000 G for about 10 to 20 minutes).

The invention also involves a method for collecting and processing blood comprising collecting whole blood in a container; centrifuging the whole blood; passing the supernatant layer of the centrifuged blood through a first porous medium, the first porous medium comprising at least one of a leucocyte depletion medium, a red cell barrier medium, and a combined leucocyte depletion red cell barrier medium; and passing the sediment layer of the centrifuged blood through a second porous medium, the second porous medium comprising a leucocyte depletion medium.

This invention may also include a method for processing a biological fluid comprising passing a biological fluid from a first container to a first porous medium comprising a red cell barrier medium, wherein the biological fluid passes in a first flow path; and passing a biological fluid from a first container to a second porous medium comprising a leucocyte depletion medium, wherein the biological fluid passes in a second flow path.

In general, donated whole blood is processed as soon as practicable in order to more effectively reduce or eliminate contaminating factors, including but not limited to leucocytes and microaggregates.

Leucocyte depletion has been heretofore typically performed during transfusion at bedside, however, in accordance with the subject invention leucocyte depletion is accomplished during the initial processing of the whole blood, which in United States practice is generally within 8 hours of collection from the donor. After the red cells have been sedimented by centrifuging, the supernatant PRP is expressed from the blood collection bag into a first satellite bag through one or more porous media which diminish the amount of leucocytes and/or block red cells, and the PRC remaining in the blood collection bag is then passed through a porous medium which removes leucocytes into a second satellite bag.

In general, using the Figures for reference, the biological fluid (e.g., donor's whole blood) is received directly into the collection bag 11. The collection bag 11, with or without the other elements of the system, may then be centrifuged in order to separate the biological fluid into a supernatant layer 31 and a sediment layer 32. After centrifugation, if whole blood is used, the supernatant layer is primarily PRP, and the sediment layer is primarily PRC. The biological fluid may be expressed from the collection bag as separate supernatant and sediment layers, respectively. There may be a clamp or the like between the collection bag 11 and the flexible tubing 25, or within the tubing, to prevent the flow of the supernatant layer from entering the wrong conduit.

Movement of the biological fluid through the system is effected by maintaining a pressure differential between the collection bag and the destination of the biological fluid (e.g., a container such as a satellite bag or a needle on the end of a conduit). The system of the invention is suitable for use with conventional devices for establishing the pressure differential, e.g., an expressor. Exemplary means of establishing this pressure differential may be by gravity head, applying pressure to the collection bag (e.g., by hand or with a pressure cuff), or by placing the other container (e.g., satellite bag) in a chamber (e.g., a vacuum chamber) which establishes a pressure differential between the collection bag and the other container. Also included within the scope of the invention may be expressors which generate substantially equal pressure over the entire collection bag.

As the biological fluid passes from one bag to the next, it may pass through at least one porous medium. Typically, if the biological fluid is the supernatant layer (e.g., PRP), it may pass from the collection bag through one or more devices or assemblies comprising one or more porous media—a leucocyte-depletion medium, a red cell barrier medium, a porous medium which combines the red cell barrier with leucocyte depletion in one porous medium, or a leucocyte depletion medium and a red cell barrier medium in series. The supernatant layer 31 is expressed from the first container 11 until flow is stopped, typically by closing a clamp in conduit 20, or automatically if the assembly includes a red cell barrier medium 12. Preferably, the supernatant layer passes through a red cell barrier medium and then through a leucocyte depletion medium. The supernatant layer is then leucocyte-depleted after passing through the leucocyte depletion medium. Additional processing, if desired, may occur downstream of the leucocyte depletion medium, either connected to the system or after being separated from the system.

The sediment layer 32 in collection bag 11 may be passed through a leucocyte depletion assembly 17 and into a container 18, such as a satellite bag. Typically, the collection bag 11, now containing primarily red cells, is then subjected to a pressure differential, as noted above, in order to prime the leucocyte depletion assembly 17 and to initiate flow.

In accordance with an additional embodiment of the invention, a method is provided whereby the recovery of various biological fluids trapped or retained in various elements of the system is maximized, either by causing a volume of gas behind the trapped or retained biological fluid to push the fluid through those elements and into the designated container, assembly, or porous medium, or by drawing the trapped or retained fluid into the designated container, assembly, or porous medium by pressure differential (e.g., gravity head, pressure cuff, suction, and the like). This provides for a more complete emptying of the container, assembly, or porous medium. Once the container is emptied completely, the flow is stopped automatically.

In order that the invention herein described may be more fully understood, the following examples are set out regarding use of the present invention. These examples are for illustrative purposes only and are not to be construed as limiting the present invention in any manner.

EXAMPLES

Example 1

The biological fluid processing system used to perform the first example includes a blood collection bag, separate PRP and PRC leucocyte depletion assemblies, as well as separate PRP and PRC satellite bags. In addition, a red cell barrier medium between the collection bag and the PRP leucocyte depletion assembly precludes the flow of red cells into the PRP satellite bag.

The red cell barrier assembly includes a porous medium for blocking flow upon contact by red cells when the PRP passes from the collecting bag. The red cell barrier assembly was preformed from 2.6 µm average diameter PBT fibers, which had been surface modified in accordance with the procedures disclosed in U.S. Pat. No. 4,880,548, using hydroxyethyl methacrylate and methacrylic acid in a monomer ratio of 0.35:1 to obtain a CWST of 95 dynes/cm and a zeta potential of −11.4 millivolts. The porous element's effective diameter was 2.31 cm, presenting a filter area of 4.2 $cm^2$, thickness was 0.051 cm, voids volume was 75% (density, 0.34 g/cc), and fiber surface area was 0.08 $m^2$.

The volume of PRP held up within the housing was <0.4 cc, representing a loss of PRP due to hold-up of less than 0.2%. The flow stopped abruptly as red cells reached the upstream surface of the red cell barrier assembly, and there was no visible evidence of red cells or hemoglobin downstream.

The PRP leucocyte depletion assembly containing a porous medium for depleting leucocytes from PRP after the PRP passed through the red cell barrier assembly, is described in U.S. Pat. No. 4,880,548. Similarly, the PRC leucocyte depletion assembly, containing a porous medium for depleting leucocytes from the unit of PRC is described in U.S. Pat. No. 4,925,572. The Example used a single unit of whole blood donated by a volunteer. The unit of blood was collected in a collection bag which was pre-filled with 63 ml of CPDA anti-coagulant. The collected blood was subjected to soft-spin centrifugation in accordance with customary blood bank practices. The collection bag was transferred, with care to avoid disturbing its contents, to a plasma extractor, which was spring biased to develop a pressure of about 90 mm Hg.

The pressure from the expressor drives the PRP from the collection bag through the red cell barrier assembly, the PRP filter assembly (where it is leucocyte depleted), and then to the satellite bag. As the PRP exited the collection bag, the interface between the PRC and PRP rose. When the red cells (present in the leading edge of the PRC layer), contacted the red cell barrier assembly, the flow was terminated, automatically, and without monitoring.

The PRC remaining in the collection bag is also processed. The collection bag is suspended and then squeezed to prime the PRC leucocyte depletion filter, and the PRC is leucocyte depleted. When the suspended collection bag is empty, the process stops automatically. The now leucocyte depleted red cell product is eventually collected in the satellite bag, and is available for transfusion into a patient as required.

The PRP previously collected in the satellite bag was then processed using normal blood bank procedures (i.e., hard-spin centrifugation) to produce PC and plasma.

Example 2

Whole blood was collected into an Adsol™ donor set and was processed under standard conditions to yield a unit of PRP. The PRP was then filtered to remove leucocytes using a filter device described in U.S. Pat. No. 4,880,548. The removal efficiency was >99.9%.

Figure 9:
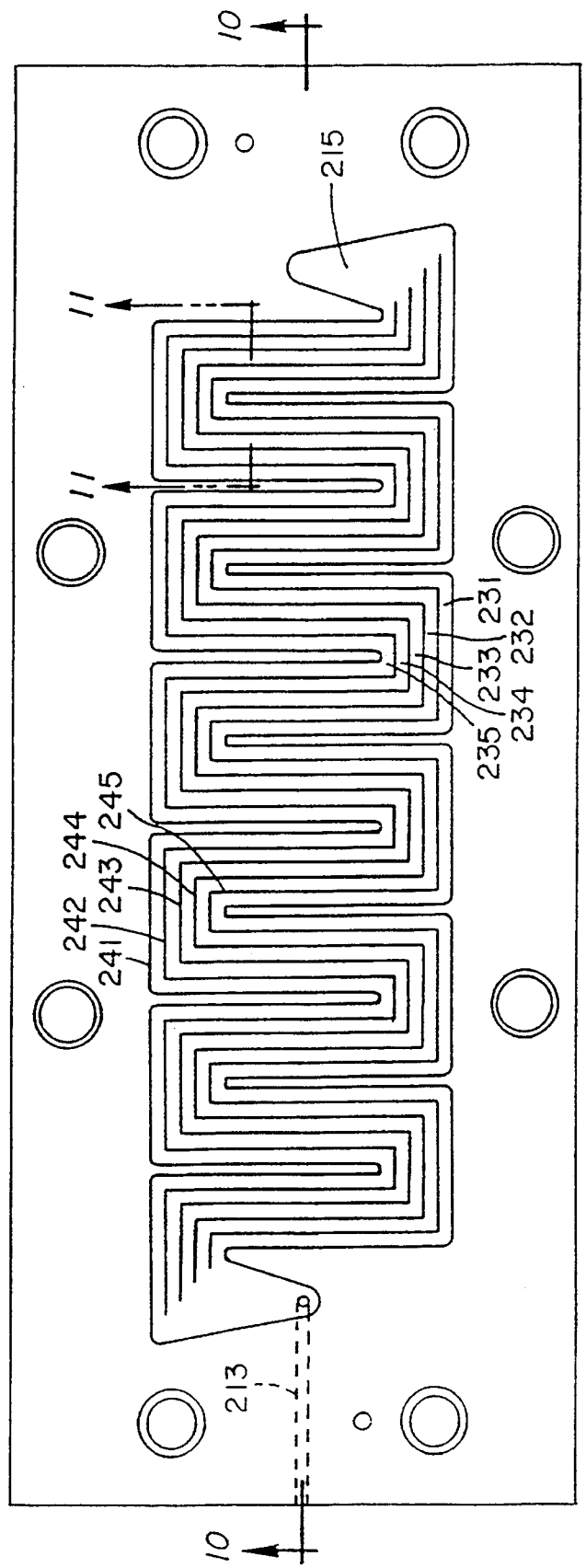
FIG. 9 is a cross-section of an embodiment of the invention, showing the second fluid flow path in a separation device according to the invention.
Figure 10:
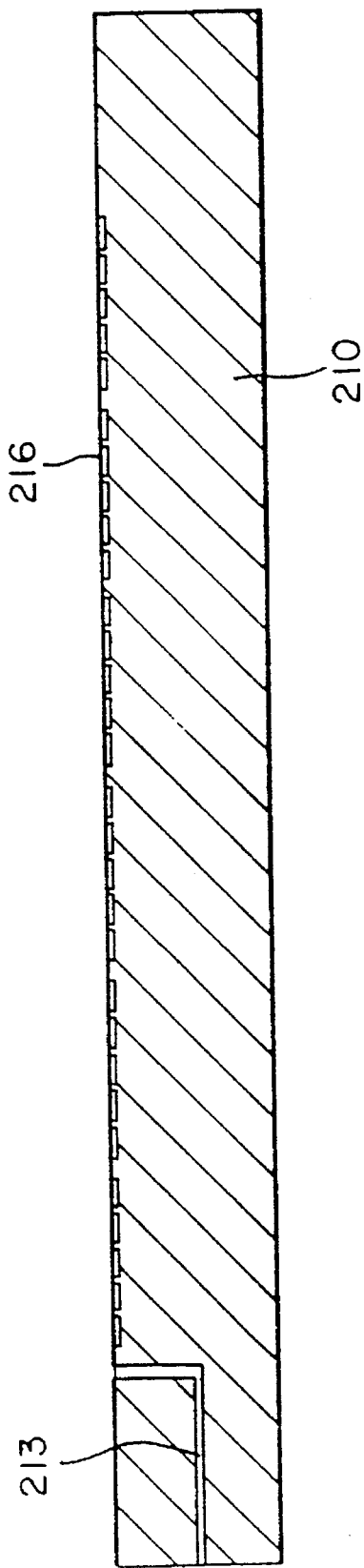
FIG. 10 is a section of FIG. 9, along C—C.

The filtered PRP unit was then placed in a pressure cuff to which a pressure of 300 mm Hg was applied. The tubing exiting the bag (clamped closed at this point) was connected to the inlet port of a separation device as shown in FIGS. 5, 6, and 9. A microporous polyamide membrane having a pore rating of 0.65 microns was used as the separation medium in the device. The area of the membrane was about 17.4 square centimeters. The depth of the first fluid flow path channels decreased from about 0.03 cm near the inlet to about 0.01 cm near the outlet. The depth of the second fluid flow path channels was about 0.025 cm. The outlet ports of the device were connected to tubing which allowed the volume of fluid exiting the device to be measured and saved for analysis.

The test of the present invention was started by opening the clamp and allowing PRP to enter the device. Clear fluid (plasma) was observed to exit one port, and turbid fluid (platelet concentrate) exited the other port. The duration of the test was 42 minutes, during which 154 ml of plasma and 32 ml of platelet concentrate was collected. The concentration of platelets in the plasma was found to be $1.2 \times 10^4/\mu l$, while the concentration of platelets in the platelet concentration was found to be $1.43 \times 10^4/\mu l$.

The above results indicate that platelets can be concentrated to a useful level and plasma can be recovered in a reasonable time by a device according to the invention.

Example 3

Whole blood was collected and processed into blood components as in example 2, and compared to that produced by conventional processing. The results comparing the blood component volumes to their respective leucocyte counts are listed in Table I, which shows the increased efficiency of leucocyte removal over the conventional procedures. Table I also reflects the increased yield of plasma and corresponding decreased yield of PRC resulting from the use of this invention.

TABLE I

|  | Conventional | Invention |
|---|---|---|
| Whole Blood volume (cc) | 450–500 | 450–500 |
| WBC · whole blood | $2 \times 10^9$ | $2 \times 10^9$ |
| PC volume (cc) | 50–65 | 50–65 |
| WBC · PC | $*1 \times 10^8$ | $*1 \times 10^5$ |
| Plasma volume (cc) | 165–215 | 170–220 |
| WBC · Plasma | $<10^8$ | $<10^8$ |
| PRC Volume (cc)* | 335 | 320 |
| WBC · PRC* | $2 \times 10^9$ | $1 \times 10^4$ |

*w/Adsol ™

Examples 4–8

The blood collection sets used to perform the examples were in general conformance with FIG. 1, without the optional red cell barrier medium assembly, and the procedure was as described earlier, using an apparatus in accordance with FIG. 4 for the first centrifuging step.

The porous medium for depleting leucocytes from PRP was performed into a cylindrical filter element 2.5 cm in diameter and 0.33 cm thick, using PBT fibers 2.6 µm in average diameter and of density 1.38 g/cc, which had been surface modified in accordance with the procedures disclosed in U.S. Pat. No. 4,880,548, using a mixture of hydroxyethyl methacrylate and methacrylic acid monomers in a weight ratio of 0.3:1. The porous medium had a CWST of 95 dynes/cm and a zeta potential of −11.4 millivolts at the pH of plasma (7.3). Fiber surface area was $0.52M^2$ and voids volume was 80%.

The porous medium for depleting leucocytes from PRC, in accordance with equations (3) and (4) above, was calculated to obtain a leucocyte depletion efficiency better than log 3 (i.e. >99.9% reduction of leucocyte content). This was accomplished by using 3.4 grams of 2.6 μm diameter PBT fiber, about 13% more fiber than called for by equations (3) and (4), and, in order to further increase the leucocyte depletion efficiency, the voids volume was decreased to 81%. These changes boosted the efficiency to better than log 4 (i.e., to >99.99%). When the PRC was expressed through this filter medium contained in a housing 6.4 cm in diameter, flow times in the desired 10 to 40 minute range were obtained at 90 mm Hg applied pressure. The fiber surfaces had been modified in the manner disclosed in U.S. Pat. No. 4,925,572, using a mixture of hydroxyethyl methacrylate and methyl methacrylate in a weight ratio of 0.27 to 1; the porous medium had a CWST of 66 dynes/cm.

The PRC porous medium described above was preceded by a pre-filter consisting of five layers of PBT melt blown web laid up in the order noted below to a total thickness of 0.25 cm:

| Grade | Weight, mg/cm$^2$ | Fiber Diameter, μm | CWST |
|---|---|---|---|
| 2.0–0.6 | .002 | 12 | 50 |
| 2.0–1.0 | .002 | 9 | 50 |
| 2.5–3.5 | .003 | 4.5 | 66 |
| 5.6–7.1 | .006 | 3.0 | 66 |
| 5.2–10.3 | .006 | 2.6 | 66 |

Each of the examples used a single unit of blood donated by a volunteer. The unit of blood was collected in a blood collection set configured as shown in FIG. 1 (without the optional red cell barrier medium assembly), the collection bag of the set having been pre-filled with 63 ml of CPDA anti-coagulant. The volume of blood collected from the various donors is shown in Column 1 of Table II. The collection set was positioned into the centrifuge bucket of FIG. 4 in accordance with customary blood bank practice, except that the PRC filter was assembled to the bracket, which in turn was mounted on the upper portion of the centrifuge bucket, thus securing the PRC filter outside and above the centrifuge bucket.

The centrifuge was then rotated at a speed that developed 2280G (at the bottom of the bucket) for 3 minutes, sufficient to cause the red blood cells to sediment into the lower portion of the collection bag. The bracket was then removed and the collection bag was transferred, with care to avoid disturbing its contents, to a plasma extractor, which was spring biased to develop a pressure of about 90 mm Hg. Breaking the seal connecting the collection bag to the PRP filter and then breaking the seal connecting the PRP filter to the satellite bag permitted the PRP supernatant layer to flow from the collection bag through the PRP filter into the satellite bag. As the PRP exited, the interface between the PRC and PRP rose in the collection bag, with flow continuing for about 10 to 20 minutes until all of the PRP had passed through the PRP filter, at which time the flow terminated abruptly and automatically as the leading edge of the PRC layer reached the PRP filter. The tubing was then clamped adjacent to the collection bag, and adjacent to the satellite bag, and the tubing between the two clamps and the PRP filter was cut. The PRP collected in the satellite bag was then processed using normal blood bank procedures to produce leucocyte-depleted PC and plasma. The volumes of PC and plasma are shown in Table II along with the number of residual leucocytes in the PC.

The collection bag, now containing only the sedimented red cells, was removed from the plasma extractor, and 100 ml of AS3 nutrient solution, which had been preplaced in the other satellite bag, was transferred into the collection bag through the PRC filter. The contents of the collection bag were then thoroughly mixed. With about 120 mm Hg pressure applied by gravity head, the PRC in the collection bag was next leucocyte-depleted by passing it through the PRC filter to the satellite bag. The PRC was now available for transfusion into a patient as required. The volume, hematocrits, and the residual leucocyte counts in the PRC are listed in Table II.

The leucocyte counts presented in the table reflect the sensitivity of the methods used for assaying the number of leucocytes residual in the PRC and in the PC effluents. No leucocytes were in fact detected in the leucocyte depleted effluents of any of the examples. Parallel experiments using more sensitive (but more laborious) assay methods indicate that the leucocyte depletion efficiencies were about ten to one hundred times better than is indicated by the data presented in the table.

TABLE II

|  | Test 1 | Test 2 | Test 3 | Test 4 | Test 5 |
|---|---|---|---|---|---|
| Whole Blood Collected (mL) | 407 | 387 | 399 | 410 | 410 |
| Whole Blood Net (%) | 45 | 42.5 | 40 | 41 | 38.5 |
| FRP Filtration Time (min.) | 16 | 11 | 14 | 15 | 19 |
| PRP Volume (mL) | 211 | 173 | 196 | 177 | 232 |
| PC volume (mL) | 47 | 52 | 49 | 69 | 61 |
| Residual WBC · PC* | $<1.0 \times 10^5$ | $<1.1 \times 10^5$ | $<1.1 \times 10^5$ | $<1.5 \times 10^5$ | $<1.3 \times 10^5$ |
| PRC Filtration Time (min.) | 15 | 18 | 11 | 11 | 12 |
| PRC Volume (mL) | 285 | 318 | 301 | 306 | 288 |
| PRC Net (%) | 64.5 | 67 | 51 | 52.5 | 60.5 |
| Residual WBC · PC* | $<7.3 \times 10^6$ | $<8.0 \times 10^6$ | $<7.5 \times 10^6$ | $<7.7 \times 10^6$ | $<7.2 \times 10^6$ |

*per unit

While the invention has been described in some detail by way of illustration and example, it should be understood that the invention is susceptible to various modifications and alternative forms, and is not restricted to the specific embodiments set forth in the Examples. It should be understood that these specific embodiments are not intended to limit the invention but, on the contrary, the intention is to cover all modifications, equivalents, and alternatives falling within the spirit and scope of the invention.

What is claimed is:

1. A biological fluid processing system comprising
   a first container;
   a second container in fluid communication with the first container;
   a third container in fluid communication with the first container;
   a first porous medium suitable for passing biological fluid therethrough interposed between the first container and the second container comprising at least one of a leucocyte depletion medium, a red cell barrier medium, and a combined leucocyte depletion red cell barrier medium;
   a second porous medium suitable for passing biological fluid therethrough interposed between the first container and the third container and comprising a leucocyte depletion medium; and,
   a first gas inlet comprising at least one porous medium for passing gas therethrough, interposed between the first container and the first porous medium, or interposed between the first container and the second porous medium.

2. The system of claim 1, further comprising a second gas inlet, said first gas inlet interposed between the first container and the first porous medium for passing biological fluid therethrough; and said second gas inlet interposed between the first container and the second porous medium for passing biological fluid therethrough.

3. The system of claim 1 further comprising an additional container in fluid communication with the second container.

4. The system of claim 1 comprising a closed sterile system.

5. The system of claim 1 wherein the gas inlet includes at least one porous medium that allows gas to pass therethrough but prevents the passage of bacteria therethrough.

6. The system of claim 5 wherein the gas inlet includes a porous medium having a pore rating of about 0.2 micrometers or less.

7. The system of claim 1 wherein the first porous medium has a CWST of greater than about 70 dynes/cm.

8. The system of claim 7 wherein the first porous medium has a CWST of greater than about 90 dynes/cm.

9. The system of claim 1 wherein the second porous medium has a CWST of greater than about 53 dynes/cm.

10. The system of claim 9 wherein the second porous medium has a CWST of greater than about 60 dynes/cm.

11. The system of claim 1 wherein the first porous medium and the second porous medium are both fibrous porous media.

12. The system of claim 1 wherein the first porous medium and the second porous medium are each capable of depleting the biological fluid of greater than 99.9% of the leukocytes in the biological fluid.

13. The system of claim 1 wherein the gas inlet includes a liquophobic membrane.

14. The system of claim 1 wherein at least one of the first porous medium and the second porous medium has a negative zeta potential.

15. The system of claim 1, further comprising a first gas outlet comprising a porous medium for passing gas therethrough, said gas outlet interposed between the first porous medium and the second container, or interposed between the second porous medium and the third container.

16. The system of claim 15, wherein the first gas outlet includes a liquophilic membrane and a liquophobic membrane.

17. A biological fluid processing system comprising
    a first container;
    a second container in fluid communication with the first container;
    a third container in fluid communication with the first container;
    a first porous medium suitable for passing biological fluid therethrough interposed between the first container and the second container comprising at least one of a leucocyte depletion medium, a red cell barrier medium, and a combined leucocyte depletion red cell barrier medium;
    a second porous medium suitable for passing biological fluid therethrough interposed between the first container and the third container and comprising a leucocyte depletion medium; and,
    a first gas outlet comprising a porous medium for passing gas therethrough, interposed between the first porous medium and the second container, or interposed between the second porous medium and the third container.

18. The system of claim 17, further comprising a second gas outlet, said first gas outlet interposed between the first porous medium for passing biological fluid therethrough and the second container; and said second gas outlet interposed between the second porous medium for passing biological fluid therethrough and the third container.

19. The system of claim 18 comprising a closed sterile system.

20. The system of claim 17 further comprising an additional container in fluid communication with the second container.

21. The system of claim 17 wherein the gas outlet includes at least one porous medium that allows gas to pass therethrough but prevents the passage of bacteria therethrough.

22. The system of claim 21 wherein the gas outlet includes a porous medium having a pore rating of about 0.2 micrometers or less.

23. The system of claim 17 wherein the first porous medium has a CWST of greater than about 70 dynes/cm.

24. The system of claim 23 wherein the first porous medium has a CWST of greater than about 90 dynes/cm.

25. The system of claim 17 wherein the second porous medium has a CWST of greater than about 53 dynes/cm.

26. The system of claim 25 wherein the second porous medium has a CWST of greater than about 60 dynes/cm.

27. The system of claim 17 wherein the first porous medium and the second porous medium are both fibrous porous media.

28. The system of claim 17 wherein the first porous medium and the second porous medium are each capable of depleting the biological fluid of greater than 99.9% of the leukocytes in the biological fluid.

29. The system of claim 17 wherein the gas outlet includes a liquophobic membrane.

30. The system of claim 29 wherein the gas outlet further comprises a liquophilic membrane.

31. The system of claim 17 wherein at least one of the first porous medium and the second porous medium has a negative zeta potential.

32. A biological fluid processing system comprising a first container;

a second container in fluid communication with the first container;

a third container in fluid communication with the first container;

a first porous fibrous medium suitable for passing biological fluid therethrough interposed between the first container and the second container comprising at least one of a leucocyte depletion medium, a red cell barrier medium, and a combined leucocyte depletion red cell barrier medium; and a second porous fibrous medium suitable for passing biological fluid therethrough interposed between the first container and the third container and comprising a leucocyte depletion medium;

the first porous fibrous medium and the second porous fibrous medium each having fibers which have an average fiber diameter of about 1 to about 4 micrometers;

wherein the system comprises a closed sterile system.

33. The system of claim 32 wherein the first porous fibrous medium and the second porous fibrous medium are each capable of depleting the biological fluid of greater than 99.9% of the leukocytes present in the biological fluid.

34. The system of claim 33 wherein the first porous fibrous medium has a CWST of greater than about 70 dynes/cm, and wherein the second porous fibrous medium has a CWST of greater than about 53 dynes/cm.

35. The system of claim 34 wherein the first porous fibrous medium has a CWST of greater than about 90 dynes/cm, and wherein the second fibrous porous medium has a CWST of greater than about 60 dynes/cm.

36. The system of claim 32 wherein the first and second porous fibrous media comprise synthetic fibers.

37. The system of claim 36 wherein the synthetic fibers comprise melt-blown fibers.

38. A method for processing blood comprising:

collecting human whole blood in a container; and, within about 8 hours of collecting the blood:

centrifuging the whole blood to form a supernatant layer and a sediment layer;

passing the supernatant layer of the centrifuged blood through a first porous medium, the first porous medium comprising at least one of a leucocyte depletion medium, a red cell barrier medium, and a combined leucocyte depletion red cell barrier medium; and passing the sediment layer of the centrifuged blood through a second porous medium, the second porous medium comprising a leucocyte depletion medium.

39. The method of claim 38 wherein centrifuging the whole blood includes separating the whole blood into a supernatant layer that includes platelets and a sediment layer that includes red blood cells; and, wherein passing the supernatant layer through the first porous medium comprises passing the centrifuged blood, supernatant layer first, through the red cell barrier medium or the combined leucocyte depletion red cell barrier medium until the first porous medium is blocked.

40. The method of claim 38 wherein passing the supernatant layer through the first porous medium depletes the supernatant layer of greater than about 99.9% of the leukocytes present in the supernatant layer.

41. The method of claim 40 wherein passing the sediment layer through the second porous medium depletes the sediment layer of greater than about 99.9% of the leukocytes present in the sediment layer.

42. The method of claim 38 wherein passing the sediment layer through the second porous medium depletes the sediment layer of greater than about 99.9% of the leukocytes present in the sediment layer.

43. The method of claim 38 wherein the method is carried out in a closed sterile blood processing system.

44. The method of claim 43 wherein passing supernatant layer through the first porous medium displaces gas, the method further comprising passing the displaced gas through a liquophobic membrane that allows the displaced gas, but not supernatant layer, to pass therethrough.

45. The method of claim 44 wherein passing gas through the liquophobic membrane includes separating gas from the blood processing system through a gas outlet.

46. The method of claim 43 wherein passing sediment layer through the second porous medium displaces gas, the method further comprising passing the displaced gas through a liquophobic membrane that allows the displaced gas, but not sediment layer, to pass therethrough.

47. The method of claim 46 wherein passing gas through the liquophobic membrane includes separating gas from the blood processing system through a gas outlet.

48. A biological fluid collection and processing system comprising a first container;

a second container in fluid communication with the first container;

a third container in fluid communication with the first container;

a first porous medium suitable for passing first biological fluid therethrough interposed between the first container and the second container comprising at least one of a leucocyte depletion medium, a red cell barrier medium, and a combined leucocyte depletion red cell barrier medium;

a second porous medium suitable for passing a second biological fluid therethrough interposed between the first container and the third container and comprising a leucocyte depletion medium; and, at least one porous medium for passing gas therethrough, that allows gas to be separated from at least one of the first biological fluid and the second biological fluid.

49. The system of claim 48 comprising a closed sterile system.

50. The system of claim 48 wherein the porous medium for passing gas therethrough comprises a liquophobic membrane.

51. A method for processing biological fluid comprising:

collecting biological fluid in a first container;

forming a supernatant layer and a sediment layer of the biological fluid;

passing the supernatant layer of the biological fluid from the first container through a first porous medium to a second container, the first porous medium comprising at least one of a leucocyte depletion medium, a red cell barrier medium, and a combined leucocyte depletion red cell barrier medium;

passing the sediment layer of the biological fluid from the first container through a second porous medium to a third container, the second porous medium comprising a leucocyte depletion medium;

the method further comprising passing gas through a gas inlet comprising a porous medium for passing gas therethrough, said gas inlet interposed between the first container and the first porous medium, or interposed between the first container and the second porous medium.

52. The method of claim 51 wherein the gas inlet is interposed between the first container and the first porous medium, the method further comprising passing gas through the gas inlet, and collecting the supernatant layer displaced by the gas into the second container.

53. The method of claim 52 comprising collecting the supernatant layer in a closed sterile system.

54. The method of claim 52 wherein an additional gas inlet comprising a porous medium for passing gas therethrough is interposed between the first container and the second porous medium, the method further comprising passing gas through the additional gas inlet, and collecting the sediment layer displaced by the gas into the third container.

55. The method of claim 52 further comprising a gas outlet comprising a porous medium for passing gas therethrough interposed between the first porous medium and the second container, the method further comprising passing gas through the gas outlet.

56. The method of claim 51 wherein the gas inlet is interposed between the first container and the second porous medium, the method further comprising passing gas through the gas inlet, and collecting the sediment layer displaced by the gas into the third container.

57. The method of claim 56 comprising collecting the sediment layer in a closed sterile system.

58. The method of claim 56 further comprising a gas outlet comprising a porous medium for passing gas therethrough interposed between the second porous medium and the third container, the method further comprising passing gas through the gas outlet.

59. A method for processing biological fluid comprising:

collecting biological fluid in a first container;

forming a supernatant layer and a sediment layer of the biological fluid;

passing the supernatant layer of the biological fluid from the first container through a first porous medium to a second container, the first porous medium comprising at least one of a leucocyte depletion medium, a red cell barrier medium, and a combined leucocyte depletion red cell barrier medium;

passing the sediment layer of the biological fluid from the first container through a second porous medium to a third container, the second porous medium comprising a leucocyte depletion medium;

the method further comprising passing gas through a gas outlet comprising a porous medium for passing gas therethrough, said gas outlet interposed between the first porous medium and the second container, or interposed between the second porous medium and the third container.

60. The method of claim 59 wherein the gas outlet is interposed between the first porous medium and the second container, the method further comprising passing gas through the gas outlet, and then collecting the supernatant layer in the second container.

61. The method of claim 60 comprising collecting the supernatant layer in a closed sterile system.

62. The method of claim 60 wherein an additional gas outlet comprising a porous medium for passing gas therethrough is interposed between the second porous medium and the third container, the method further comprising passing gas through the additional gas outlet, and then collecting the sediment layer in the third container.

63. The method of claim 59 wherein the gas outlet is interposed between the second porous medium and the third container, the method further comprising passing gas through the gas outlet, and then collecting the sediment layer in the third container.

64. The method of claim 63 comprising collecting the sediment layer in a closed sterile system.

* * * * *